(12) United States Patent
Okamura

(10) Patent No.: US 10,302,929 B2
(45) Date of Patent: May 28, 2019

(54) FLUORESCENCE MICROSCOPY APPARATUS

(71) Applicant: OLYMPUS CORPORATION, Hachioji-shi, Tokyo (JP)

(72) Inventor: Toshiro Okamura, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/007,070

(22) Filed: Jun. 13, 2018

(65) Prior Publication Data

US 2018/0292637 A1 Oct. 11, 2018

Related U.S. Application Data

(63) Continuation of application No. PCT/JP2015/085251, filed on Dec. 16, 2015.

(51) Int. Cl.
*G01N 21/01* (2006.01)
*G02B 21/16* (2006.01)
*G01N 21/64* (2006.01)
*G02B 21/06* (2006.01)
(Continued)

(52) U.S. Cl.
CPC .............. *G02B 21/16* (2013.01); *G01N 21/01* (2013.01); *G01N 21/64* (2013.01); *G01N 21/6458* (2013.01); *G02B 6/0011* (2013.01); *G02B 21/06* (2013.01); *G02B 21/361* (2013.01); *G02B 21/365* (2013.01); *G01N 2021/6463* (2013.01)

(58) Field of Classification Search
CPC ..................................................... G01N 21/01
See application file for complete search history.

(56) References Cited

U.S. PATENT DOCUMENTS 6,437,345 B1 * 8/2002 Bruno-Raimondi .......................
G01N 21/474
250/252.1
7,812,303 B2 10/2010 Meyers et al.
(Continued)

FOREIGN PATENT DOCUMENTS

| JP | 05236206 A | 9/1993 |
| JP | 5639654 B2 | 10/2010 |
| JP | 2015530618 A | 10/2015 |

OTHER PUBLICATIONS

International Preliminary Report on Patentability (IPRP) and Written Opinion (and English langauage translation thereof) dated Jun. 19, 2018 issued in International Application No. PCT/JP2015/0852512.

(Continued)

*Primary Examiner* — Yara B Green
(74) *Attorney, Agent, or Firm* — Holtz, Holtz & Volek PC

(57) ABSTRACT

An illumination device irradiates a sample with excitation light spatially modulated according to a two-dimensional pattern while temporally varying the pattern. A plate-shaped first optical member has a light receiving face that faces the sample face, receives fluorescence light emitted from the sample via the light receiving face, and guides the fluorescence light in a direction that is in parallel with the light receiving face. A photodetector receives the fluorescence light guided by the first optical member, and outputs a detection signal. A fluorescence image of the sample is generated using the detection signal and an intensity distribution formed on the sample face due to the excitation light acquired for every pattern.

17 Claims, 17 Drawing Sheets

(51) Int. Cl.
*G02B 21/36* (2006.01)
*F21V 8/00* (2006.01)

(56) References Cited

U.S. PATENT DOCUMENTS

| | | |
|---|---|---|
| 8,053,715 B2 | 11/2011 | Meyers et al. |
| 9,007,433 B2 | 4/2015 | Ozcan et al. |
| 9,581,548 B2 | 2/2017 | Cooper et al. |
| 2009/0118622 A1* | 5/2009 | Durkin ................ A61B 5/0073 600/473 |
| 2010/0140458 A1 | 6/2010 | Meyers et al. |
| 2010/0214404 A1* | 8/2010 | Chen ................ G02B 21/0032 348/79 |
| 2010/0294916 A1 | 11/2010 | Meyers et al. |
| 2015/0241351 A1 | 8/2015 | Cooper et al. |

OTHER PUBLICATIONS

International Search Report (ISR) (and English language translation thereof) dated Mar. 1, 2016 issued in International Application No. PCT/JP2015/085251.

Ferri, et al., "Longitudinal coherence in thermal ghost imaging", Applied Physics Letter 92, 261109, Jul. 1, 2008.

Katz, et al., "Compressive Ghost Imaging", Applied Physics Letters 95, 131110, Sep. 30, 2009.

Shibuya, et al., "The study of biological imaging by circulatory pattern ghost imaging microscopy", 2014.

Tian, et al., "Fluorescence ghost imaging with pseudothermal light", Optics Letters, Aug. 15, 2011, vol. 36, No. 16, pp. 3302-3304.

* cited by examiner

FIG. 9A

|  | x=1 | x=2 | x=3 |
|---|---|---|---|
| y=1 | $T_1$ | $T_2$ | $T_3$ |
| y=2 | $T_4$ | $T_5$ | $T_6$ |
| y=3 | $T_7$ | $T_8$ | $T_9$ |

FIG. 9B

| $t_1$ | | | |
|---|---|---|---|
| | $I_{11}$ | $I_{12}$ | $I_{13}$ |
| | $I_{14}$ | $I_{15}$ | $I_{16}$ |
| | $I_{17}$ | $I_{18}$ | $I_{19}$ |

FIG. 9C

| $t_M$ | | | |
|---|---|---|---|
| | $I_{M1}$ | $I_{M2}$ | $I_{M3}$ |
| | $I_{M4}$ | $I_{M5}$ | $I_{M6}$ |
| | $I_{M7}$ | $I_{M8}$ | $I_{M9}$ |

FIG. 9D

| $T_{GI1}$ | $T_{GI2}$ | $T_{GI3}$ |
|---|---|---|
| $T_{GI4}$ | $T_{GI5}$ | $T_{GI6}$ |
| $T_{GI7}$ | $T_{GI8}$ | $T_{GI9}$ |

FLUORESCENCE MICROSCOPY APPARATUS

BACKGROUND OF THE INVENTION

1. Field of the Invention

The present invention relates to a fluorescence microscopy apparatus.

2. Description of the Related Art

Fluorescence microscopy apparatus configured to observe cell shapes, cell compositions, and the like, is used in various fields such as the research field, the medical field, and the like. As such conventional fluorescence microscopy apparatus, lens-based fluorescence microscopes have become mainstream.

In recent years, the development of lens-free fluorescence microscopy apparatuses has been advancing. For example, Patent document 1 (Japanese Patent No. 5,639,654) discloses a lens-free system that is capable of acquiring a holographic image and a fluorescence image at the same time. This system is configured using a fluorescence excitation light source, a holographic light source, a spatial filter, an image sensor, and a prism.

Image observation devices employing ghost imaging have been proposed in Patent documents 2 and 3 (U.S. Pat. No. 8,053,715 B2, U.S. Pat. No. 8,242,428 B2) and Non-patent document 1 (F. Ferri, D. Magatti, V. G. Sala and A. Gatti, "Longitudinal coherence in thermal ghost imaging", Appl. Phys. Let. 92, 261109 (2008)) and document 2 (Ori Katz, Yaron Bromberg, and Yaron Silberberg, "Compressive ghost imaging", Appl. Phys. Let. 95, 131110 (2009).).

In ghost imaging, an object is irradiated with excitation light subjected to random spatial modulation while temporally varying the excitation light. The object light emitted from the object is measured as bucket light having no spatial information. Subsequently, an object image is reproduced based on the correspondence between the spatial distribution of the excitation light and the bucket light.

SUMMARY OF THE INVENTION

The present invention has been made in view of such a situation. Accordingly, it is an exemplary purpose of an embodiment of the present invention to provide a fluorescence microscopy apparatus employing a ghost imaging method.

An embodiment of the present invention relates to a fluorescence microscopy apparatus structured to measure a fluorescence image of a sample held by a sample holder. The fluorescence microscopy apparatus comprises: an illumination device structured to emit light spatially modulated according to a two-dimensional pattern onto the sample while temporally varying the pattern; a first optical member having a light receiving face that faces a sample face, and structured to receive a fluorescence light emitted from the sample via the light receiving face, and to guide the fluorescence light in a direction that is in parallel with the light receiving face; and a photodetector structured to receive the fluorescence light guided by the first optical member, and to output a detection signal. The detection signal and an intensity distribution formed on the sample face due to an excitation light are acquired for every pattern, and are used to generate the fluorescence image of the sample.

Another embodiment of the present invention also relates to a fluorescence microscopy apparatus. The fluorescence microscopy apparatus comprises: a sample holder structured to hold the sample via a sample face thereof; an illumination device structured to emit an excitation light spatially modulated according to a two-dimensional pattern onto the sample while temporally varying the pattern; and a light receiving unit structured to receive a fluorescence light emitted from the sample. The illumination device, the sample holder, and the light receiving unit are arranged such that an output face of the illumination device, the sample face, and a light receiving face of the light receiving unit are arranged in parallel and overlap.

Yet another embodiment of the present invention relates to an incubator (culture apparatus). The incubator comprises multiple built-in fluorescence microscopy apparatuses according to any one of the aforementioned embodiments.

It should be noted that any desired combinations of the aforementioned components may be made, and representation of the present invention may be mutually substituted between a method, apparatus, system, and so forth, which are also effective as an embodiment of the present invention.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIGS. 9A through 9D are diagrams for explaining compressive ghost imaging;

DETAILED DESCRIPTION OF THE INVENTION

Figure 1:
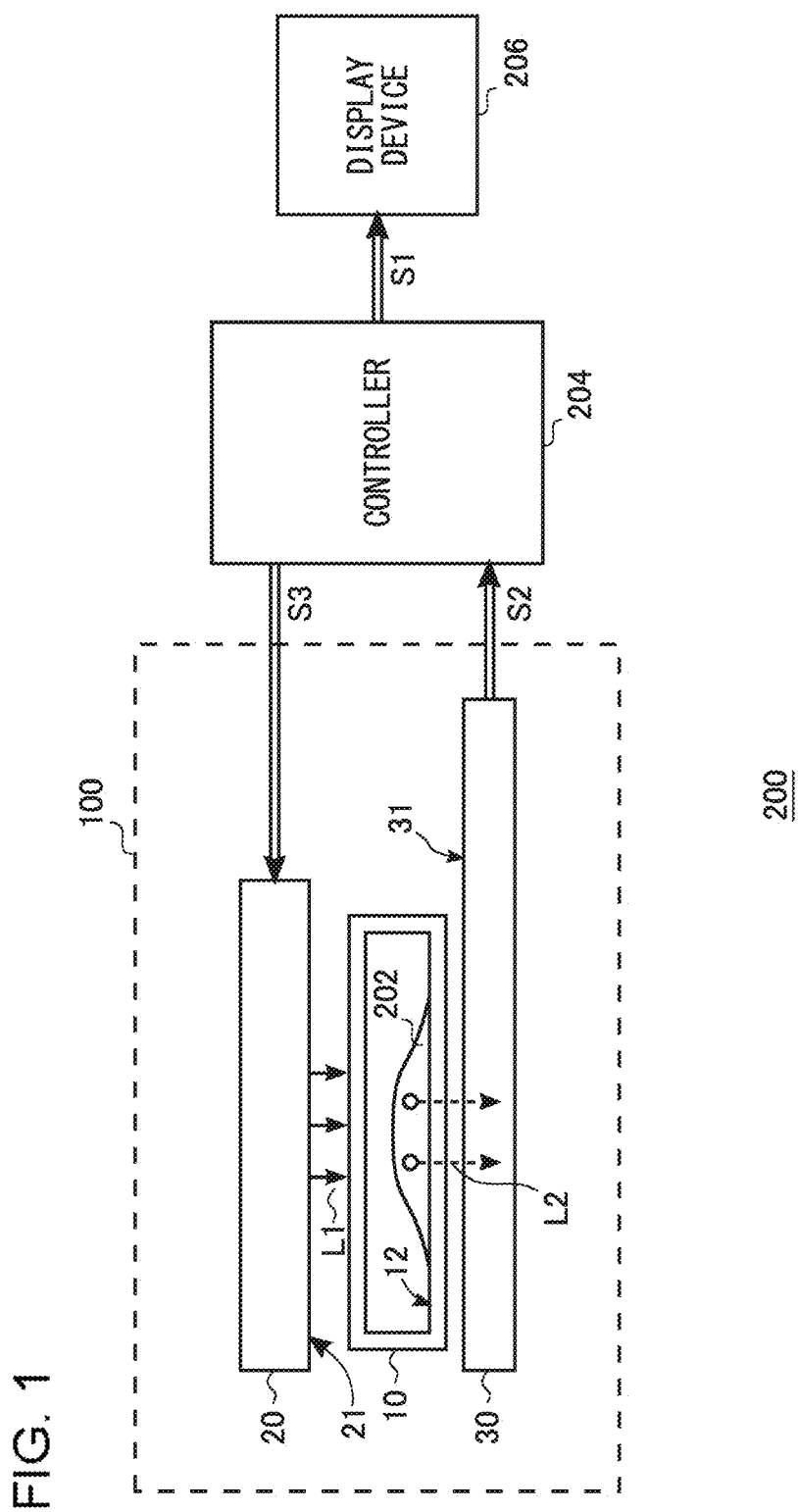
FIG. 1 is a diagram showing a fluorescence microscopy apparatus.

First, description will be made regarding the outline of several embodiments according to the present invention. An embodiment of the present invention relates to a fluorescence microscopy apparatus structured to measure a fluorescence image of a sample held by a sample holder. The fluorescence microscopy apparatus comprises: an illumination device structured to emit light spatially modulated according to a two-dimensional pattern onto the sample while temporally varying the pattern; a first optical member having a light receiving face that faces a sample face, and structured to receive fluorescence light emitted from the sample via the light receiving face, and to guide the fluorescence light in a direction that is in parallel with the light receiving face; and a photodetector structured to receive the fluorescence light guided by the first optical member, and to output a detection signal. The detection signal and an intensity distribution formed on the sample face due to the excitation light are acquired for every pattern, and are used to generate the fluorescence image of the sample.

With such an embodiment of the present invention, by configuring the light receiving unit structured to measure the bucket light as a combination of the plate-shaped first optical member and the photodetector, this arrangement allows the light receiving unit to have a small thickness (small height). This allows the fluorescence microscopy apparatus to have a small thickness. In addition, or otherwise alternatively, this arrangement is capable of relaxing constraints imposed on the layout of the photodetector that measures the bucket light. It should be noted that, in the present specification, in addition to a case in which the light receiving face of the first optical member directly faces the sample face, "face each other" also includes a case in which another optical element (e.g., a filter or a polarizing element) or the like is arranged between them such that they indirectly face each other.

Also, the first optical member may comprise a waveguide grating structured to selectively couple with the fluorescence light.

Also, the first optical member may comprise a light guide plate having a back face that is provided with a reflection layer structured to selectively reflect the fluorescence light.

Also, the first optical member may be arranged on a side that is opposite to the illumination device across the sample holder.

Also, the first optical member may be arranged between the sample holder and the illumination device, and may be structured to allow the excitation light to pass through.

Also, the illumination device may comprise: an excitation light source structured to emit an excitation light in a direction that is in parallel with the sample face; a second optical member having a slab waveguide extending substantially in parallel with the sample face, and structured to receive the excitation light via an input face thereof, and to emit the excitation light in the form of a plane wave in a direction that is orthogonal to a direction in which the excitation light is guided; and a spatial modulator arranged between an output face of the second optical member and the sample holder, and structured to spatially modulate the excitation light configured as the plane wave. Also, the second optical member may comprise a waveguide grating. This also allows the illumination device to have a thin structure. This allows the fluorescence microscopy apparatus itself to have a further reduced thickness.

Also, the illumination device may comprise an array of light-emitting elements each having an output face which is in parallel with the sample face, and each structured to emit an excitation light which is independently modulated. Also, the light-emitting element may comprise a VCSEL (Vertical Cavity Surface Emitting LASER). This also allows the illumination device to have a thin structure. This allows the fluorescence microscopy apparatus itself to have a further reduced thickness.

Also, the intensity distribution formed on the sample face due to the excitation light may be obtained by calculation based on a pattern supplied to the spatial light modulator. This arrangement does not require an optical system for measuring the intensity distribution on the sample face. This allows the fluorescence microscopy apparatus to have a further reduced size.

The fluorescence microscopy apparatus according to an embodiment may further comprise an image sensor arranged on a side that is opposite to the illumination device across the sample holder and the first optical member, and structured to measure a two-dimensional intensity distribution of the light modulated due to the sample. Also, the first optical member may allow the light modulated due to the sample to pass through. Also, an output of the image sensor may be used to generate a holographic image of the sample. With this embodiment, both a holographic image and a fluorescence image can be acquired.

Also, the light modulated due to the sample may be the excitation light that has passed through the sample. With this embodiment, a single excitation light source can be shared as an excitation light source for generating a holographic image and as an excitation light source for generating a fluorescence image. This allows the device to have a further simplified configuration.

Another embodiment of the present invention also relates to a fluorescence microscopy apparatus. The fluorescence microscopy apparatus comprises: a sample holder structured to hold the sample via a sample face thereof; an illumination device structured to emit an excitation light spatially modulated according to a two-dimensional pattern onto the sample while temporally varying the pattern; and a light receiving unit structured to receive fluorescence light emitted from the sample. The illumination device, the sample holder, and the light receiving unit are arranged such that an output face of the illumination device, the sample face, and a light receiving face of the light receiving unit are arranged in parallel and overlap.

Also, the light receiving unit may be arranged on a side that is opposite to the illumination device across the sample holder, and is structured to be transparent for the excitation light. Also, the fluorescence microscopy apparatus may further comprise an image sensor arranged on a side that is opposite to the illumination device across the sample holder and the light receiving unit, and structured to measure a two-dimensional intensity distribution of the excitation light modulated due to the sample.

Yet another embodiment of the present invention relates to a fluorescence microscopy system. The fluorescence microscopy system may comprise: any one of the aforementioned fluorescence microscopy apparatuses; and a processor arranged as an external component of the fluorescence microscopy apparatus. The processor may generate a fluorescence image of the sample using the detection signal and the intensity distribution output from the fluorescence microscopy apparatus. With yet another embodiment, the processor may be provided as a built-in component of the fluorescence microscopy apparatus.

Description will be made below regarding the present invention based on preferred embodiments with reference to the drawings. The same or similar components, members, and processes are denoted by the same reference numerals, and redundant description thereof will be omitted as appropriate. The embodiments have been described for exemplary purposes only, and are by no means intended to restrict the present invention. Also, it is not necessarily essential for the present invention that all the features or a combination thereof be provided as described in the embodiments.

FIG. 1 is a diagram showing a fluorescence microscopy apparatus 100 according to an embodiment. FIG. 1 shows a fluorescence microscopy system 200 including the fluorescence microscopy apparatus 100 and peripheral components thereof. In some drawings, a beam of light is represented by a single line, and an electric signal line is represented by a double line. The fluorescence microscopy system 200 generates an image of a sample 202 that emits fluorescence light according to excitation light. The sample 202 is not restricted in particular. For example, the sample 202 may include cells or a fluorescent protein.

The fluorescence microscopy system 200 includes the fluorescence microscopy apparatus 100, a controller 204, and a display device 206. The controller 204 controls the overall operation of the fluorescence microscopy system 200, and generates a fluorescence image S1 based on a signal received from the fluorescence microscopy apparatus 100. The display device 206 displays the fluorescence image S1 thus generated. Also, the display device 206 is provided as a user interface.

A cross-sectional view of the fluorescence microscopy apparatus 100 is shown in FIG. 1. The fluorescence microscopy apparatus 100 mainly includes a sample holder 10, an illumination device 20, and a light receiving unit 30. The sample holder 10 holds the sample 202. From a certain point of view, a face of the sample 202 to be observed can be referred to as a "sample face 12". Also, a virtual flat surface assuming that the sample 202 is configured as such a flat surface may be regarded as the sample face 12. In a case in which the sample 202 has a non-negligible thickness, the sample face 12 may be set to a flat surface including a part of the sample 202. From another point of view, the face of the sample 202 via which the sample 202 is mounted on the sample holder 10 may be regarded as the sample face 12. In other words, it can be understood that the sample holder 10 holds the sample 202 via the sample face 12 thereof. The sample holder 10 preferably holds the sample 202 on the horizontal face in order to prevent deformation of the sample 202 due to gravity. However, in a case in which deformation of the sample 202 does not occur or otherwise does not readily occur, the sample holder 10 is not restricted to such an arrangement.

The illumination device 20 emits excitation light L1 spatially modulated according to a two-dimensional pattern onto the sample 202 while temporally varying the two-dimensional pattern. The illumination device 20 spatially modulates the excitation light L1 based on a pattern control signal S3 received from the controller 204. Phase modulation, amplitude modulation, or a combination thereof, may be employed as such spatial modulation. The waveform of the excitation light L1 is selected based on the excitation waveform required for a fluorescent protein.

The light receiving unit 30 receives, via its light receiving face 32, fluorescence light L2 emitted from the sample 202, and generates a detection signal S2 that corresponds to an amount of received light. In the ghost imaging method, the light receiving unit 30 is also referred to as a "bucket detector". The detection signal S2 generated by the light receiving unit 30 has no spatial resolution, i.e., is configured as a signal obtained by spatially accumulating (integrating) the fluorescence light emitted from the sample 202. The light receiving unit 30 is configured to be sensitive to the fluorescence waveform emitted from a fluorescent protein.

The illumination device 20, the sample holder 10, and the light receiving unit 30 are arranged such that the output face 21 of the illumination device 20, the sample face 12, and the light receiving face 31 of the light receiving unit 30 are aligned in parallel such that they overlap. The illumination device 20, the sample holder 10, and the light receiving unit 30 are each configured as a combination of plate-shaped members.

The controller 204 sequentially switches a pattern to be supplied to the illumination device 20. With such an arrangement, the controller 204 acquires a fluorescence image of the sample 202 based on the detection signal S2 received from the light receiving unit 30 acquired for every pattern and an intensity distribution on the sample face formed due to the excitation light L1. The image generating algorithm employed in the controller 204 will be described later.

The above is the basic configuration of the fluorescence microscopy apparatus 100. The present invention encompasses various kinds of apparatuses that can be regarded as a configuration shown in FIG. 1, or otherwise that can be derived from the aforementioned description. That is to say, the present invention is not restricted to a specific configuration. More specific description will be made below regarding an example configuration for clarification and ease of understanding of the essence of the present invention and the circuit operation. That is to say, the following description will by no means be intended to restrict the technical scope of the present invention.

First Embodiment

Figure 2:
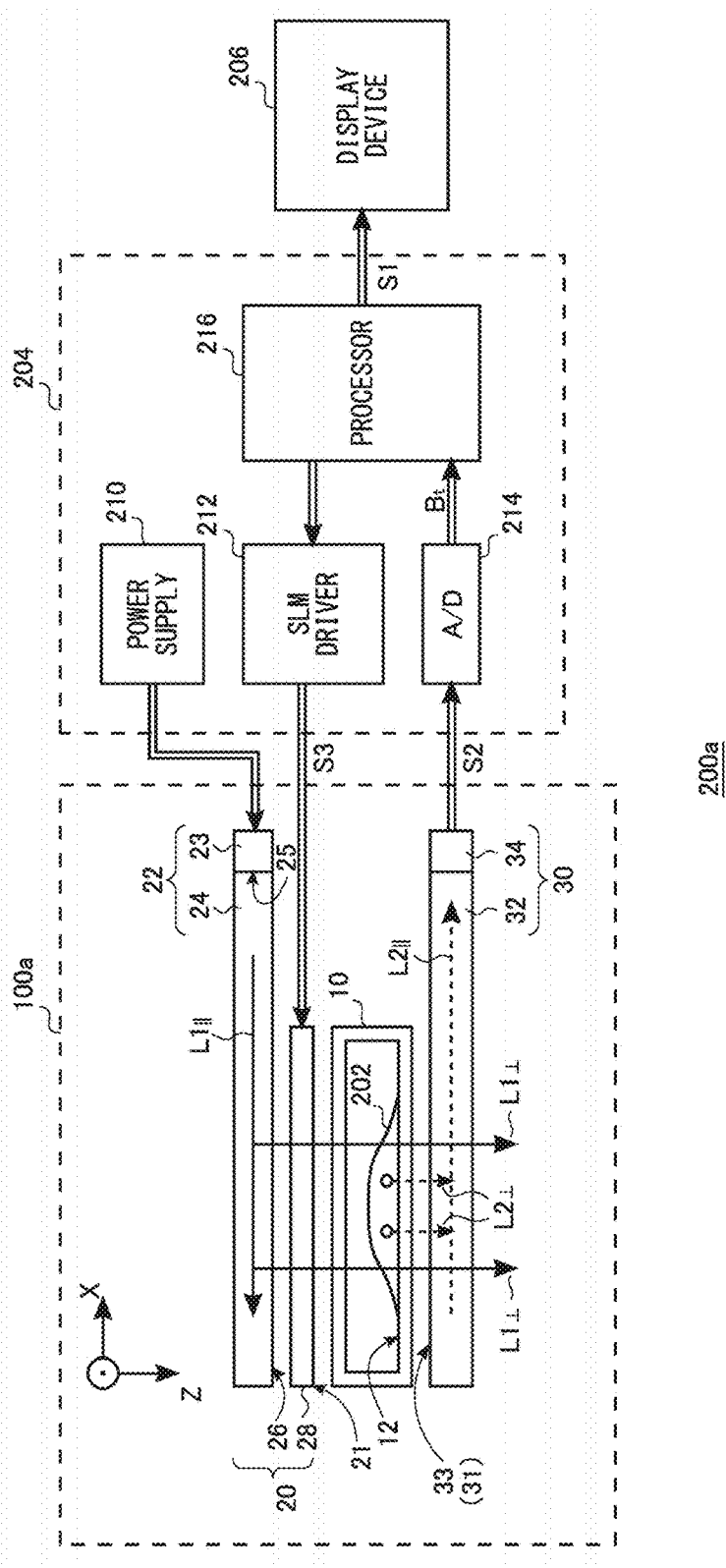
FIG. 2 is a diagram showing a fluorescence microscopy system including a fluorescence microscopy apparatus according to a first embodiment.

FIG. 2 is a diagram showing a fluorescence microscopy system 200a including a fluorescence microscopy apparatus 100a according to a first embodiment. In the following description, for ease of understanding and simplicity of description, the X, Y, and Z directions will be defined as shown in the drawings. That is to say, the Z-axis is defined as an axis extending toward the lower side in the vertical direction, and the XY plane will be defined as a plane extending along the horizontal plane. The sample face 12 is aligned in parallel with the XY plane. The illumination device 20 emits excitation light $L1_\perp$ in the Z-axis direction. It should be noted that the appended suffix "$\perp$" appended to the beam of light represents light that propagates in the Z-axis direction (or otherwise in the reverse direction thereof). The appended suffix "$\parallel$" represents light that propagates in parallel with the XY plane.

The light propagates through the illumination device 20, the sample holder 10, and the light receiving unit 30 in this order. Description will be made below regarding the light receiving unit 30 and the illumination device 20 in this order.

Light Receiving Unit (30)

In the first embodiment, the light receiving unit 30 includes a first optical member 32 and a photodetector (photoreceptor element) 34. The first optical member 32 is configured to have a plate structure, and has a light receiving face 33 configured to receive fluorescence light $L2_\perp$ emitted from the sample 202. The first optical member 32 guides the fluorescence light $L2_\perp$ thus received such that it propagates in a direction (X-axis direction) that is in parallel with the light receiving face 33. The first optical member 32 is arranged such that its light receiving face 33 faces the sample face 12. The light receiving face 33 and the sample face 12 are preferably aligned in parallel. However, the layout is not restricted to such an arrangement. The light receiving face 33 of the first optical member 32 corresponds to the light receiving face 31 of the light receiving unit 30. The photodetector 34 is arranged such that the light receiving face 35 thereof is in parallel with the YZ plane, and is configured to receive fluorescence light $L2_\parallel$ guided by the first optical member 32. As the photodetector 34, a photodiode may be employed, for example. However, the photodetector 34 is not restricted to such an arrangement. In the present embodiment, the first optical member 32 is arranged on a side opposite to the illumination device 20 across the sample holder 10.

An output signal of the photodetector 34 is input to the controller 204 as the detection signal S2. An A/D converter 214 of the controller 204 converts the detection signal S2 into a digital value $B_t$, and inputs the digital value $B_t$ to a processor 216. In a case in which the photodetector 34 includes a built-in A/D converter, and is configured to have a digital output, the A/D converter 214 may be omitted.

The processor 216 controls the fluorescence microscopy apparatus 100a, and performs processing for generating a fluorescence image. The display device 206 displays a fluorescence image. Furthermore, the display device 206 is used as an interface for operating the fluorescence microscopy system 200a. The processor 216 may be configured as a dedicated hardware component. Also, the processor 216 may be configured as a computer or a workstation. The processor 216 may be provided as a separate component external to the fluorescence microscopy apparatus 100a. Also, the processor 216 may be built into the fluorescence microscopy apparatus 100a together with an SLM driver 212 or the A/D converter 214.

Figure 3A:
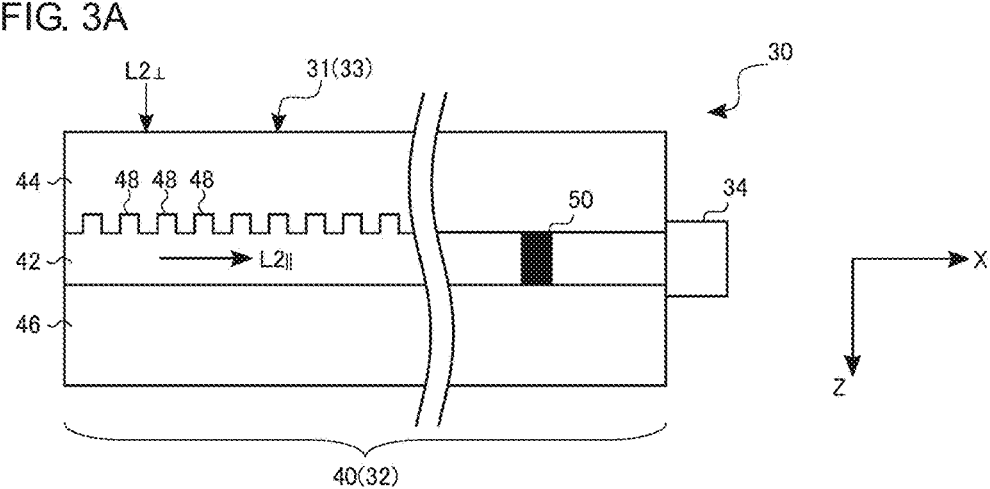
FIGS. 3A and 3B are a plan view and a cross-sectional view of a light receiving unit including an input waveguide grating, respectively, according to a first example configuration.
Figure 3B:
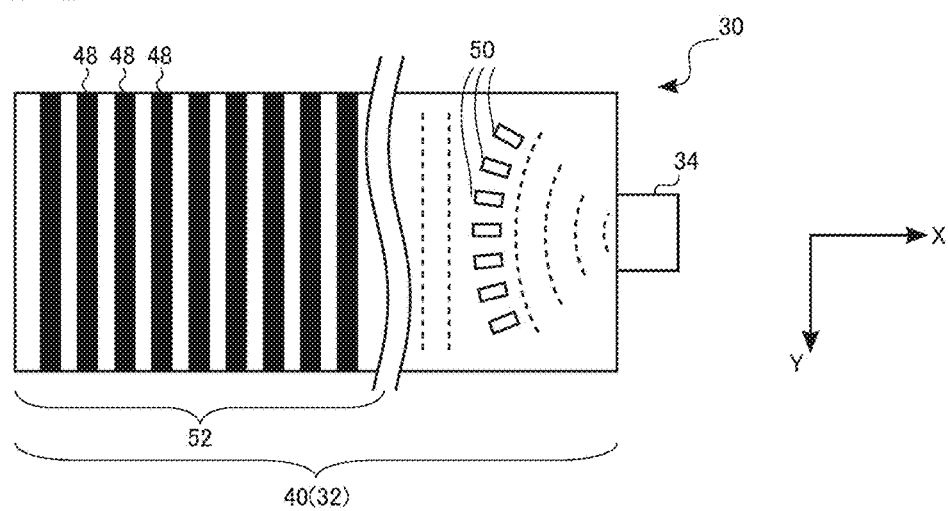

As the first optical member 32, a waveguide grating (which will be referred to as the "input waveguide grating") described below may be employed. The input waveguide grating is configured to selectively couple with the fluorescence light $L2_\perp$, and not to couple with the excitation light $L1_\perp$. FIGS. 3A and 3B are respectively a plan view and a cross-sectional view each showing the light receiving unit 30 including the input waveguide grating 40 according to a first example configuration. The slab input waveguide grating 40 includes a core layer 42, and includes an upper cladding layer 44 and a lower cladding layer 46 arranged such that the core layer 42 is interposed between them. A large number of grating grooves 48 are formed in a boundary between the upper cladding layer 44 and the core layer 42 (or otherwise in a boundary between the core layer 42 and the lower cladding layer 46) at predetermined intervals such that they extend in the Y-axis direction. The input waveguide grating array 40 receives, via the light receiving face 31, the fluorescence light $L2_\perp$ that propagates in the Z-axis direction. The input waveguide grating 40 couples with the fluorescence light $L2_\perp$, and guides the fluorescence light thus coupled as the fluorescence light $L2_\parallel$ in the X-axis direction. The fluorescence light $L2_\parallel$ is input to the photodetector 34 arranged at the end portion of the input waveguide grating 40.

Figure 4A:
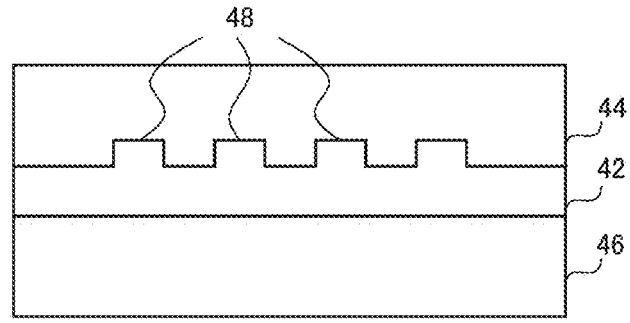
FIGS. 4A through 4D are cross-sectional diagrams each showing grooves of a grating.
Figure 4B:
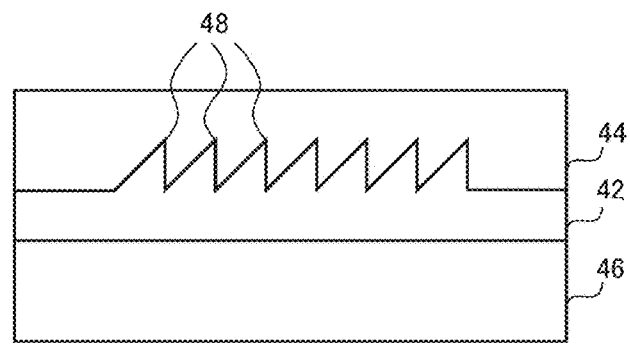
Figure 4C:
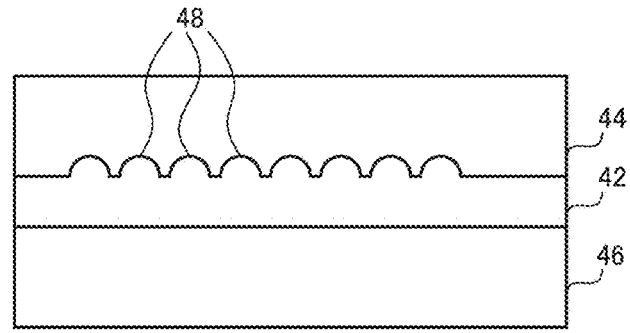
Figure 4D:
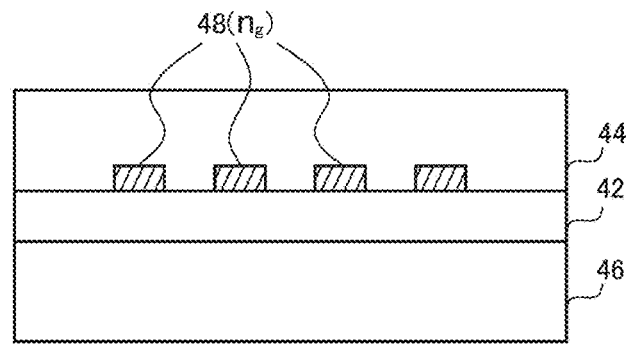

FIGS. 4A through 4D are cross-sectional diagrams each showing grooves of the grating. The grating grooves 48 may have a rectangular groove structure as shown in FIG. 4A, a sawtooth-shaped groove structure as shown in FIG. 4B, or a wave-shaped groove structure as shown in FIG. 4C. Also, as shown in FIG. 4D, the grating grooves 48 may be formed of a material having a different refractive index $n_g$.

Figure 5:
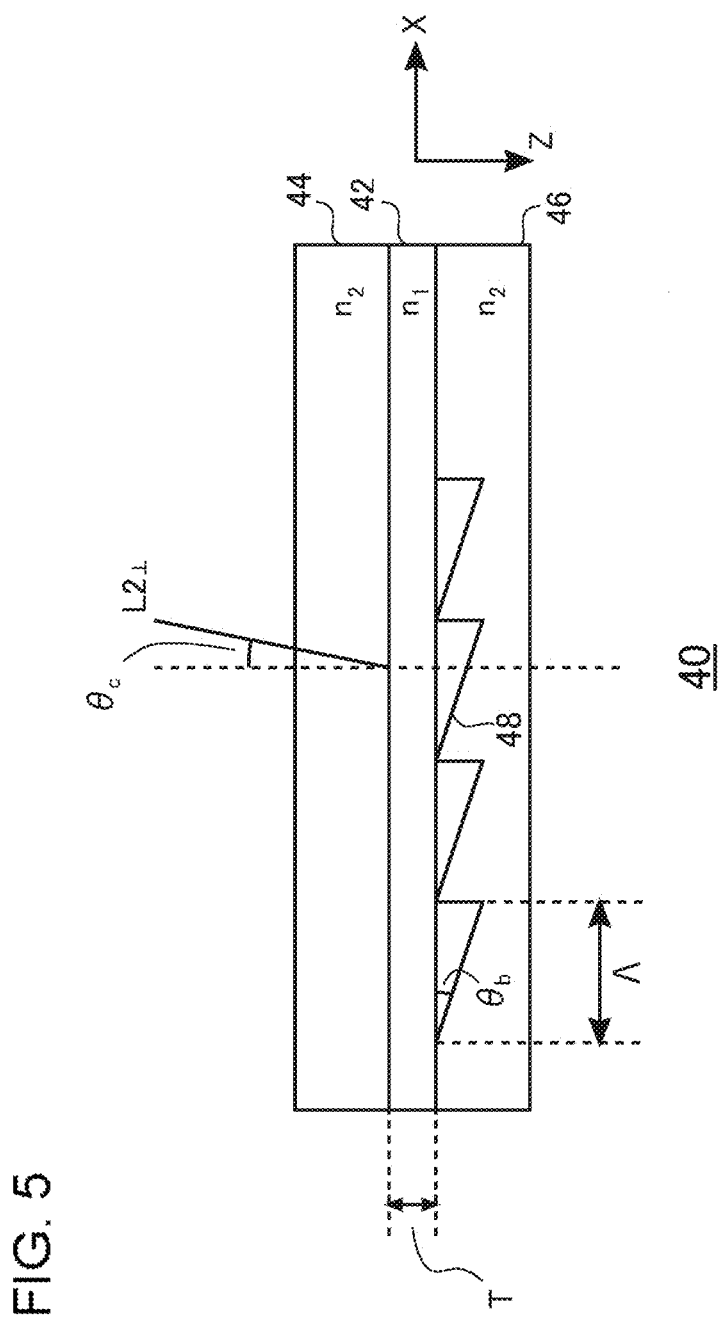
FIG. 5 is a cross-sectional diagram showing an input waveguide grating.

Description will be made regarding an example design of the input waveguide grating 40. FIG. 5 is a cross-sectional view of the input waveguide grating 40. Description will be made regarding an example employing a sawtooth-shaped groove structure shown in FIG. 4B.

$\wedge$: Grating period
$\theta_b$: Grating blaze angle
$n_1$: Refractive index of core layer 42
$n_2$: Refractive index of upper cladding layer 44 and lower cladding layer 46
T: Thickness of core layer 42
$\theta_c$: Incident angle of fluorescence light L2

In order to guide the fluorescence light $L2_\parallel$ thus coupled to the photodetector 34 with high efficiency, an arrangement is preferably configured to prevent the fluorescence light $L2_\parallel$ that is being guided in the X-axis direction from leaking from the light receiving face 31 or otherwise from a face opposite to the light receiving face 31. In order to provide such a function, the input waveguide grating 40 is configured to provide one-beam coupling (which will also be referred to as "single-beam coupling"). The condition for providing the one-beam coupling is represented by the following Expressions with the equivalent refractive index as N.

$$\theta_{in} = \sin^{-1}(N/n_1) \tag{1}$$

$$\theta_b = (\theta_{in} + \theta_c)/2 \tag{2}$$

Here, regarding the waveguide, the following general expressions hold true.

$$n_2 \cdot k_0 \cdot \sin(\theta_c) = \beta + q \cdot k \tag{3}$$

$$q = 0, \pm 1, \pm 2,$$

$$\beta = N \cdot k_0$$

$$K = 2\pi/\wedge$$

Description will be made assuming that the fluorescence wavelength $\lambda_2 = 0.520$ μm, $n_2 = 1.494$, $n_1 = 1.544$, T=0.55 μm, and $\wedge = 0.342$ μm. In this case, the equivalent refractive index N is 1.523. By substituting these values into Expression (3), it can be understood that, when $q=-1$, $\theta_c$ becomes 0. In this case, the fluorescence light $L2_\perp$ input in an incident direction that is orthogonal to the light receiving face 31 is coupled. Here, $\theta_{in} = 80.539°$ holds true based on Expression (1). Thus, it can be understood that $\theta_b$ is preferably set to 40.270° based on Expression (2).

The equivalent refractive index N is 1.524 when the excitation waveform $\lambda_1 = 0.490$ μm. In this case, when $q=-1$, $\theta_c = 3.42°$ holds true. When $q=-2$, $\theta_c = -64.25°$ holds true. The excitation light $L1_\perp$ is input in an incident direction that is substantially orthogonal to the light receiving face 31 (i.e., with an angle $\theta_c=0°$. Accordingly, the excitation light $L1_\perp$ does not couple with the input waveguide grating 40. That is to say, the excitation light $L1_\perp$ passes through the input waveguide grating 40. The above is a description of the wavelength selectivity provided by the input waveguide grating 40.

Returning to FIG. 3, in a case in which the photodetector 34 has a small width as compared with the width of the input waveguide grating 40 in the Y-axis direction, the guided light is preferably focused on the photodetector 34. Accordingly, a conversion grating 50 may be formed between the photodetector 34 and a region 52 in which the grating grooves 48 are formed. The conversion grating 50 converts the guided light $L2_\parallel$ configured as a plane wave into a spherical wave. This allows the photodetector 34 thus employed to have a small width.

Figure 6:
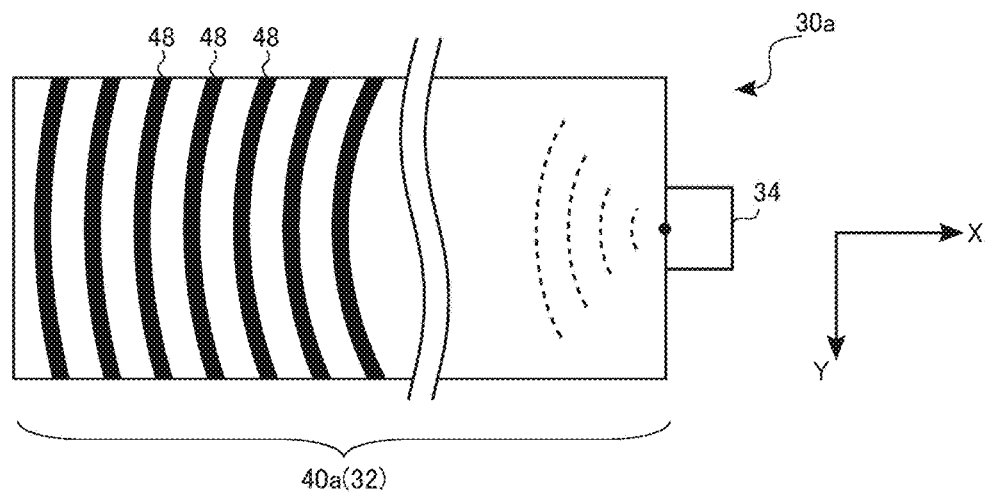
FIG. 6 is a plan view showing a light receiving unit including an input waveguide grating according to a second example configuration.

It should be noted that the configuration of the input waveguide grating 40 is not restricted to such an arrangement shown in FIGS. 3A and 3B. FIG. 6 is a plan view of the light receiving unit 30a including an input waveguide grating 40a according to a second example configuration. In this example, the conversion grating 50 shown in FIG. 3 is omitted. Instead, the grating grooves 48 are each formed in a circular shape concentric with the photodetector 34. The grating grooves 48 guide the light received via the light receiving face 31 in the X direction while converting the guided light into a spherical wave, thereby focusing the guided light on the photodetector 34.

Illumination Device (20)

Returning to FIG. 2, description will be made regarding a configuration of the illumination device 20. The illumination device 20 includes a thin flat-panel light source 22 and a spatial light modulator (SLM) 28. The flat-panel light source 22 emits excitation light $L1_\perp$ having a uniform intensity and a uniform phase via the output face 26 thereof. The spatial light modulator 28 is configured as a transmissive spatial light modulator. The spatial light modulator 28 is arranged such that it is interposed between the sample holder 10 and the output face 26 of the flat-panel light source 22 (i.e., the output face of a second optical member 24 described later). The spatial light modulator 28 spatially modulates the excitation light $L1_\perp$ configured as a plane wave. A pattern to be used for the spatial modulation is controlled according to the pattern control signal S3 received from the controller 204. An SLM driver 212 of the controller 204 switches the pattern to be supplied to the spatial light modulator 28 in a random (pseudo-random) manner. The excitation light L1 provided with a spatially random pattern by the spatial light modulator 28 is also referred to as "speckle".

Figure 7:
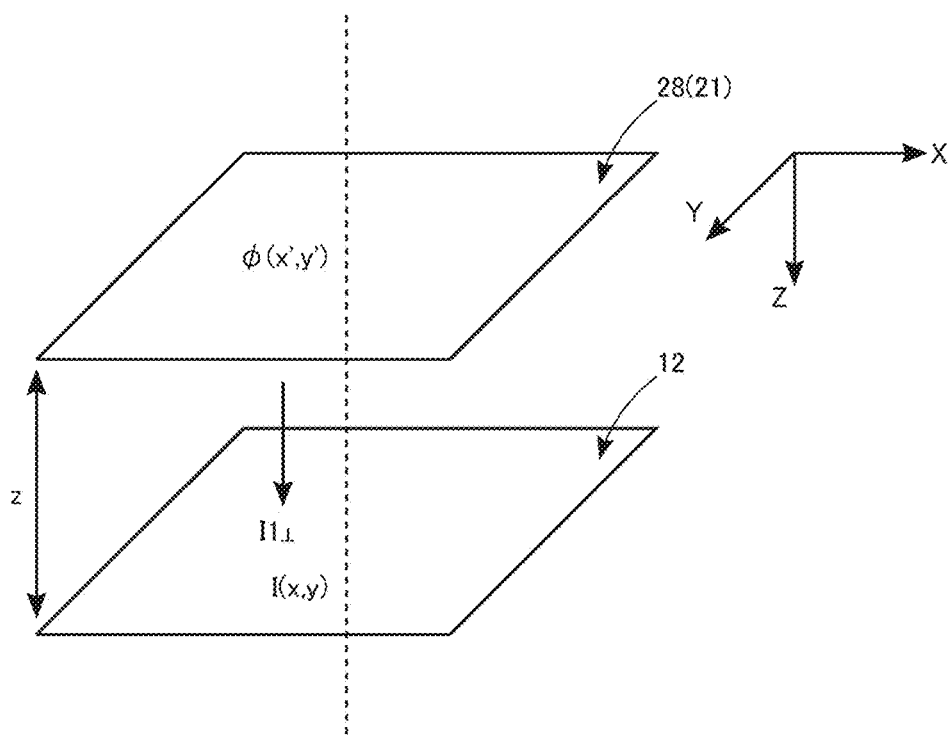
FIG. 7 is a diagram for explaining phase modulation performed by a spatial light modulator.

Description will be made below assuming that the spatial light modulator 28 is configured as a phase modulator that applies phase modulation. By changing the phase distribution of the excitation light L1, this arrangement is capable of changing the spatial intensity distribution formed on the sample face 12 due to the excitation light L1. FIG. 7 is a diagram for explaining phase modulation performed by the spatial light modulator shown in FIG. 7.

On the flat surface of the spatial light modulator 28 (i.e., the output face 21 of the illumination device 20), the phase distribution provided by the phase modulator is represented by $\phi(x', y')$. Furthermore, the spatial light modulator 28 and the sample face 12 are arranged at an interval of the distance z. In this state, the intensity distribution I(x, y) formed on the sample face 12 is calculated.

Immediately after the light passes through the spatial light modulator 28, the complex amplitude of the light g(x', y') is represented by Expression (4).

$$g(x', y') = \exp\left(\frac{i2\pi}{\lambda}\varphi(x', y')\right) \quad (4)$$

The complex amplitude of the light on the sample face 12, i.e., f(x, y), is represented by Expression (5) based on a Fresnel integral expression.

$$f(x, y) = \left(\frac{1}{i \cdot \lambda \cdot z}\right) \int g(x', y') \exp\left(\frac{i2\pi}{\lambda}\left(z + \frac{(x'-x)^2 + (y'-y)^2}{2 \cdot z}\right)\right) dx' dy' \quad (5)$$

It should be noted that Expression (5) is obtained using approximation assuming that z is large to some extent. However, f(x, y) may be calculated without using such approximation.

The intensity distribution I(x, y) formed on the sample face 12 is represented by Expression (6).

$$I(x,y)=f(x,y)\cdot f^*(x,y) \quad (6)$$

Here, "*" represents a complex conjugate.

As described above, the intensity distribution formed on the sample face 12 due to the excitation light $L1_\perp$ can be obtained by calculation based on the pattern supplied to the spatial light modulator 28. That is to say, with such an arrangement, there is no need to split the excitation light $L1_\perp$, and there is no need to input the split excitation light to a different arm in order to measure the intensity distribution thereof.

Returning to FIG. 2, the flat-panel light source 22 preferably includes an excitation light source 23 and a second optical member 24. The excitation light source 23 emits excitation light $L1_\parallel$ that is in parallel with the sample face 12. A power supply 210 included in the controller 204 supplies power to the excitation light source 23. FIG. 2 shows an example in which the excitation light $L1_\parallel$ is emitted from the excitation light source 23 toward the negative side in the X-axis direction. Also, the excitation light $L1_\parallel$ may be emitted in the X-axis direction or in the Y-axis direction (or otherwise toward the negative side in the Y-axis direction). As the excitation light source 23, a semiconductor laser may be employed. The second optical member 24 has a slab waveguide arranged substantially in parallel with the sample face 12. The second optical member 24 receives the excitation light $L1_\parallel$ from the excitation light source 23 via its input face 25, and outputs the excitation light $L1_\perp$ via its output face 26 as a plane wave in a direction that is orthogonal to the direction in which the excitation light $L1_\parallel$ propagates. The second optical member 24 may be configured using a waveguide grating (which will be referred to as the "output waveguide grating" or "radiation waveform grating") in the same manner as the first optical member 32.

Figure 8A:
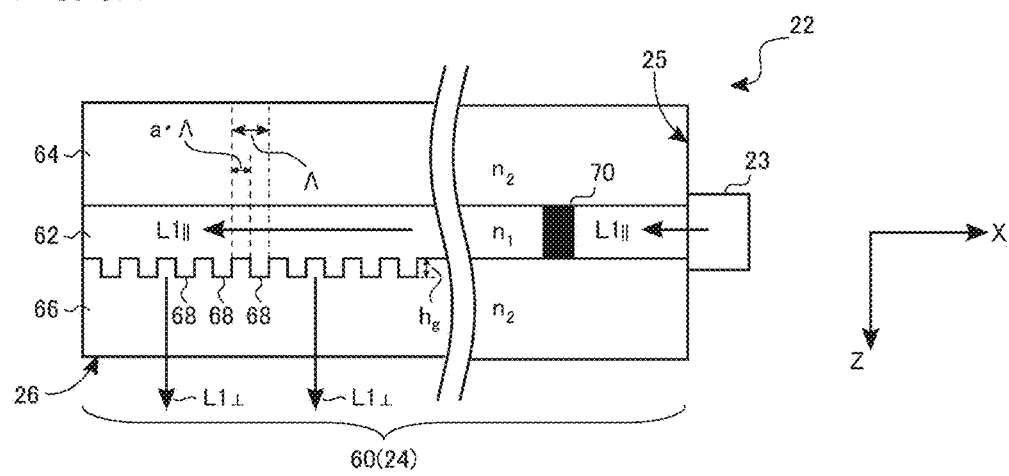
FIGS. 8A and 8B are a plan view and a cross-sectional view, respectively, of a flat-panel light source including an output waveguide grating.
Figure 8B:
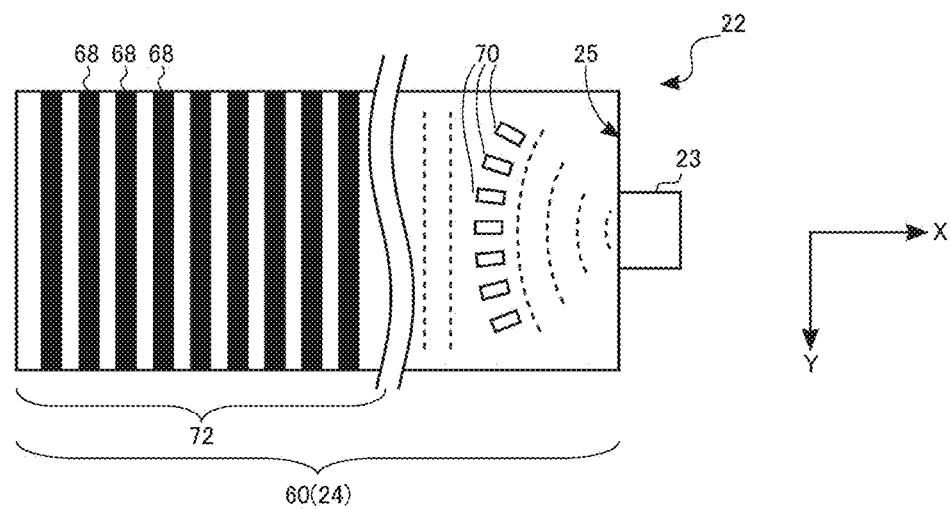

FIGS. 8A and 8B are plan view and a cross-sectional diagram, respectively, each showing the flat-panel light source 22 including an output waveguide grating 60. The slab output waveguide grating 60 includes a core layer 62, and includes an upper cladding layer 64 and a lower cladding layer 66 arranged such that the core layer 62 is interposed between them. A large number of grating grooves 68 are formed in a boundary between the lower cladding layer 66 and the core layer 62 (or otherwise in a boundary between the upper cladding layer 64 and the core layer 62) at predetermined intervals such that they extend in the Y-axis direction. In these drawings, the grating grooves 68 each having a rectangular shape are shown. Here, "$h_g$" represents the height (depth) of each groove, and "a" represents the grating factor (a<1). The output waveguide grating 60 receives the excitation light $L1_\parallel$ emitted from the excitation light source 23 onto the input face 25 toward the negative side in the X-axis direction. The output waveguide grating 60 couples with the excitation light $L1_\parallel$ thus received, and outputs the excitation light $L1_\perp$ via the output face 26 while guiding the coupled excitation light $L1_\parallel$ toward the negative side in the X-axis direction. It should be noted that the conversion grating 70 may be formed between the excitation light source 23 and a region 72 in which the grating grooves 68 are formed. The conversion grating 70 converts the excitation light $L1_\parallel$ emitted from the excitation light source 23 in the form of a spherical wave into a plane wave, and guides the excitation light thus converted to the region 72.

Description will be made regarding an example design of the output waveguide grating 60. The aforementioned Expression (3) holds true for the output waveguide grating 60. Description will be made assuming that the excitation waveform $\lambda_1$=0.490 μm, $n_2$=1.494, $n_1$=1.544, T=0.55 μm, $\wedge$=0.322 μm, a=0.5, and $h_g$=50 nm. In this case, the equivalent refractive index N is 1.524. By substituting these values into Expression (3), it can be understood that, when q=−1, $\theta_c$ becomes 0. In this case, this arrangement is capable of emitting the excitation light $L1_\perp$ in a direction that is orthogonal to the output face 26.

It should be noted that, by changing the grating factor a and the height $h_g$ of each groove, this arrangement is capable of controlling the illumination area and the luminance intensity (uniformity) in the X-axis direction. In a case in which the grooves have a constant height $h_g$, the intensity of light emitted from the output face 26 can decay in an exponential manner with progression toward the negative side in the X-axis direction. In the usage of the fluorescence microscopy apparatus 100, subsequent calculation requires correction. Accordingly, in some cases, such an arrangement is undesirable. In order to solve such a problem, by gradually increasing the height $h_g$ of each groove with progression toward the negative side in the X-axis direction, this arrangement is capable of emitting the excitation light $L1_\perp$ onto the sample 202 with high uniformity over the range in the X-axis direction.

It should be noted that the output waveguide grating 60 may include a grating having a concentric structure in the same manner as the input waveguide grating 40a shown in FIG. 6. Also, the groove structures shown in FIGS. 4A through 4D may be employed. That is to say, the groove structure is not restricted in particular.

The above is the configuration of the fluorescence microscopy apparatus 100a according to the first embodiment. Next, description will be made regarding the operation thereof.

The processor 216 changes the pattern of the phase $\phi(x, y)$ to be supplied to the spatial light modulator 28 for every time period $t_1, t_2, \ldots, t_M$. Furthermore, the processor 216 calculates the intensity distributions $I_1(x, y), I_2(x, y), \ldots, I_M(x, y)$ on the sample face 12 for every time point (for every time period).

Furthermore, the light receiving unit 30 measures the fluorescence light $L2_\perp$ acquired corresponding to the intensity distribution for each time period, and generates the detection signal S2 that represents the bucket light. The A/D converter 214 converts the detection signal S2 thus acquired for every time period (exposure period) into digital values $B_1, B_2, \ldots, B_M$. It should be noted that description will be made assuming that the sample 202 is stationary over a series of measurement periods. In other words, the measurement time is required to be set within a period in which the sample 202 is assumed to be stationary.

The processor 216 reproduces a fluorescence image of the sample 202 based on $I_1(x, y), I_2(x, y), I_M(x, y)$, and $B_2, B_2, \ldots, B_M$, acquired in a series of measurements. This reproduction is performed using a ghost imaging method.

The fluorescence image $T_{GI}(x, y)$ on the sample face 12 can be calculated based on the following Expression (7).

$$T_{GI}(x,y)=1/M \times \Sigma_{j=1:M}(B_j - <B>)I_j(x,y) \quad (7)$$

Here, "$<B>$" represents an ensemble average of the M measurement values $B_1$ through $B_M$.

The processor 216 may calculate the fluorescence image $T_{GI}(x, y)$ based on Expression (7). However, such calculation requires a sufficiently large sample number M (M≥N). Here, "N" represents the number of pixels of the fluorescence image. In a case in which x=1, 2, …, $x_{MAX}$, and y=1, 2, …, $y_{MAX}$, N is represented by $N=x_{MAX} \times y_{MAX}$. For example, in a case in which $x_{MAX}=y_{MAX}=300$, i.e., N=90,000 pixels, and the spatial light modulator 28 has a processing speed of 120 Hz, this arrangement requires a total measurement time of 750 seconds. In some usages, such a measurement time is excessively long.

In order to solve such a problem, the processor 216 may calculate the fluorescence image $T_{GI}(x, y)$ using a compressive ghost imaging algorithm described below.

In compressive ghost imaging, directing attention to the fact that an image acquired in nature has a feature (tendency) of being sparse, the fluorescence image $T_{GI}$ is reproduced based on a small number of samples M(<N) after imposing a certain constraint on the fluorescence image $T_{GI}$.

FIGS. 9A through 9D are diagrams for explaining the compressive ghost imaging. For simplicity of calculation, the pixel number j is defined by j=x+XMAX×(y−1). Here, j=1, 2, …, N. For simplicity of description, FIG. 9A shows an example in which $x_{MAX}=y_{MAX}=3$, and M=2. FIG. 9A shows an actual image T. FIGS. 9B and 9C show the intensity distributions $I_1$ and $I_M$ of the excitation light on the sample face 12 at different time points $t_1$ and $t_M$, respectively. FIG. 9D shows the fluorescence image $T_{GI}$ reproduced based on the compressive ghost imaging. All the images each include N (9) pixels. The compressive ghost imaging can be understood as an algorithm for calculating the fluorescence image $T_{GI}$ that is close to the actual image T using a small number M of samples.

Each image is represented by a one-dimensional vector (column vector) having N elements. When a given fluorescence image $T_{GI}$ is assumed, the bucket light $d_t$ acquired at the time point t is represented by Expression (8).

$$\begin{bmatrix} d_1 \\ \vdots \\ d_t \\ \vdots \\ d_M \end{bmatrix} = \begin{bmatrix} I_{11} & I_{12} & \cdots & I_{19} \\ I_{21} & I_{22} & & I_{29} \\ \vdots & \vdots & \ddots & \vdots \\ I_{M1} & I_{M2} & \cdots & I_{M9} \end{bmatrix} \begin{bmatrix} T_{GI1} \\ T_{GI2} \\ \vdots \\ T_{GI9} \end{bmatrix} \quad (8)$$

The bucket light that corresponds to the actual image is measured as the measurement value B. Accordingly, when the difference between $d_t$ and $B_t$ becomes the minimum (zero), it can be assumed that the reproduced image $T_{GI}$ matches the actual image T. Thus, in the compressive ghost imaging, $T_{GI}$ with a minimum error calculated based on the following Expression (9) is a solution to be acquired.

$$\Sigma_{t=1:M}(d_t-B_t)^2 \quad (9)$$

In the compressive ghost imaging, the transformation operator $\Psi$ is introduced. Here, "$\Psi$" is an operator that transforms a matrix into a sparse matrix. Here, "$\Psi$" may represent disperse cosine transformation (DCT). The aforementioned fact that an image acquired in nature has a feature of being sparse corresponds to a small primary norm of a matrix transformed by the operator $\Psi$ as represented by Expression (10). Here, "$|\ |_{L1}$" represents the primary norm.

$$|\Psi\{T_{GI}\}|_{L1} \quad (10)$$

An error amount is defined by Expression (11) using a certain weighting coefficient $\alpha$. By acquiring the image $T_{GI}$ such that the error amount thus defined becomes a minimum value, this arrangement provides an image that is similar to the actual image T.

$$\Sigma_{t=1:M}(d_t-B_t)^2+\alpha|\Psi\{T_{GI}\}|_{L1} \quad (11)$$

Figure 10A:
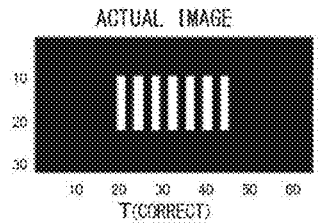
FIGS. 10A through 10E are diagrams showing calculation steps of the compressive ghost imaging.
Figure 10B:
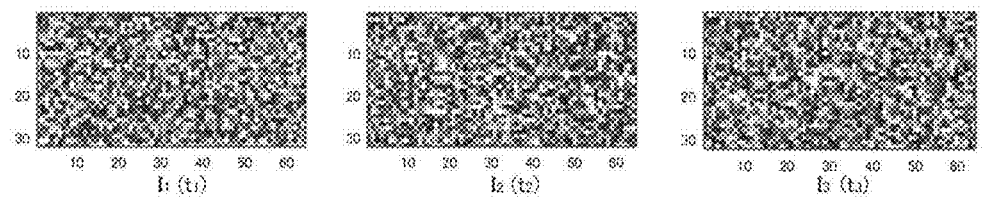
Figure 10C:
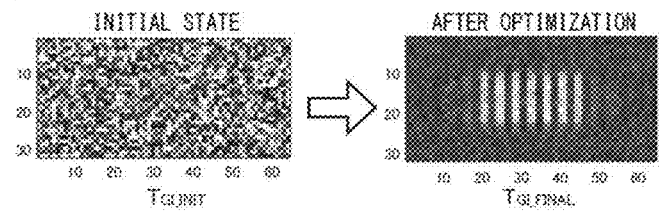
Figure 10D:
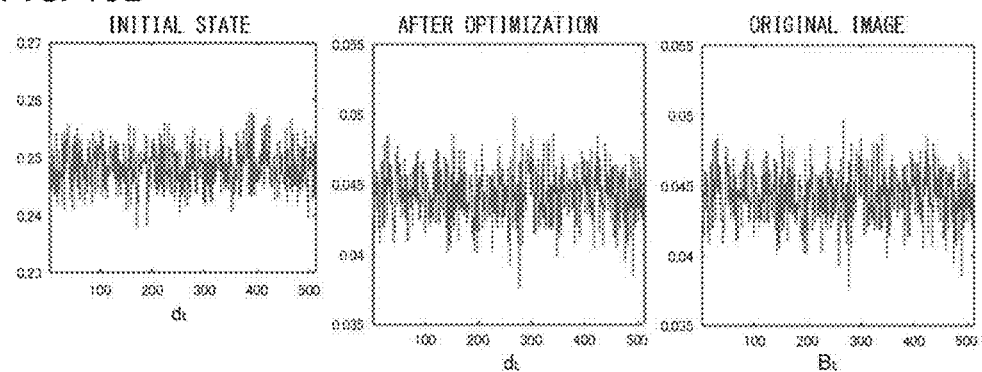
Figure 10E:
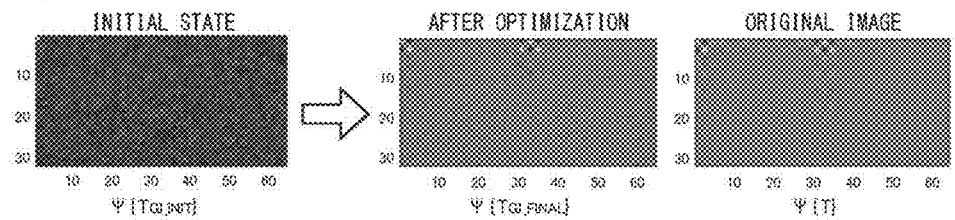

FIGS. 10A through 10E are diagrams showing calculation steps of the compressive ghost imaging. Description will be made regarding an example in which M=512, $x_{MAX}$=64, and $y_{MAX}$=32. FIG. 10 shows an actual image T to be obtained. FIG. 10B shows the intensity distributions $I_1$, $I_2$, and $I_3$ of the excitation light on the sample face 12 at the time points $t_1$, $t_2$, and $t_3$. FIG. 10C shows an image $T_{GI\_INIT}$ before optimization (in the initial state) and an image $T_{GI\_FINAL}$ after optimization (in the final state). FIG. 10D shows the bucket light $d_{t\_INIT}$ acquired based on the image $T_{GI\_INIT}$ before optimization (in the initial state), the bucket light $d_{t\_FINAL}$ acquired based on the optimized image $T_{GI\_FINAL}$, and the bucket light $B_t$ acquired based on the actual image T. FIG. 10E shows an image $\Psi(T_{GI\_INIT})$ obtained by performing DCT on the image $T_{GI\_INIT}$ before optimization (in the initial state), an image $\Psi(T_{GI\_FINAL})$ obtained by performing DCT on the optimized image $T_{GI\_INIT}$, and an image $\Psi(T)$ obtained by performing DCT on the actual image T.

First, the initial value $T_{GI\_INIT}$ of $T_{GI}$ is generated in a random manner. As shown in FIG. 10E, the image $\Psi(T_{GI})$ obtained by performing DCT of the initial value image $T_{GI\_INIT}$ exhibits a high-density distribution, i.e., is not sparse. In contrast, the image $\Psi(T)$ obtained by performing DCT of the actual image T exhibits a low-density distribution, i.e., is sparse.

Furthermore, as shown in FIG. 10D, the waveform of $d_t$ obtained based on the initial image $T_{GI\_INIT}$ diverges from the waveform of the bucket light $B_t$ acquired based on the actual image. Correction of the image $T_{GI}$ so as to minimize the error amount represented by Expression (11) means that the image $\Psi(T_{GI})$ is adjusted such that it becomes sparse, and such that the calculation value $d_t$ of the bucket light is adjusted such that it becomes closer to the bucket light $B_t$ that corresponds to the actual image. By repeatedly performing this correction, the optimized image $T_{GI}$ becomes a restoration of the actual image $T_j$.

The above is the operation of the fluorescence microscopy apparatus 100a. Next, description will be made regarding the advantages thereof.

With the fluorescence microscopy apparatus 100a according to the first embodiment, the input waveguide grating 40 is employed in the light receiving unit 30. Instead of acquiring spatial information with respect to light, the input waveguide grating 40 is capable of acquiring a spatially integrated value thereof, thereby allowing the input waveguide grating 40 to have a very thin structure. In the ghost imaging method, the bucket light measurement does not require such spatial information, and requires only such a spatially integrated value. Accordingly, it can be said that the input waveguide grating 40 is very suitable as a bucket detector employed in ghost imaging. With the fluorescence microscopy apparatus 100a according to the first embodiment, by employing the input waveguide grating 40, this arrangement allows the light receiving unit 30 to have a thin structure as compared with an arrangement employing an image-focusing optical system such as a lens, mirror, or the like, or otherwise a prism. This allows the fluorescence microscopy apparatus 100a to have a thin structure (small height).

With the fluorescence microscopy apparatus 100a, a waveguide grating is employed as the second optical member 24 of the flat-panel light source 22. This allows the thickness of the illumination device 20 in the height direction to be reduced regardless of the thickness of the excitation light source 23. This allows the thickness of the fluorescence microscopy apparatus 100a to be further reduced.

Second Embodiment

Figure 11:
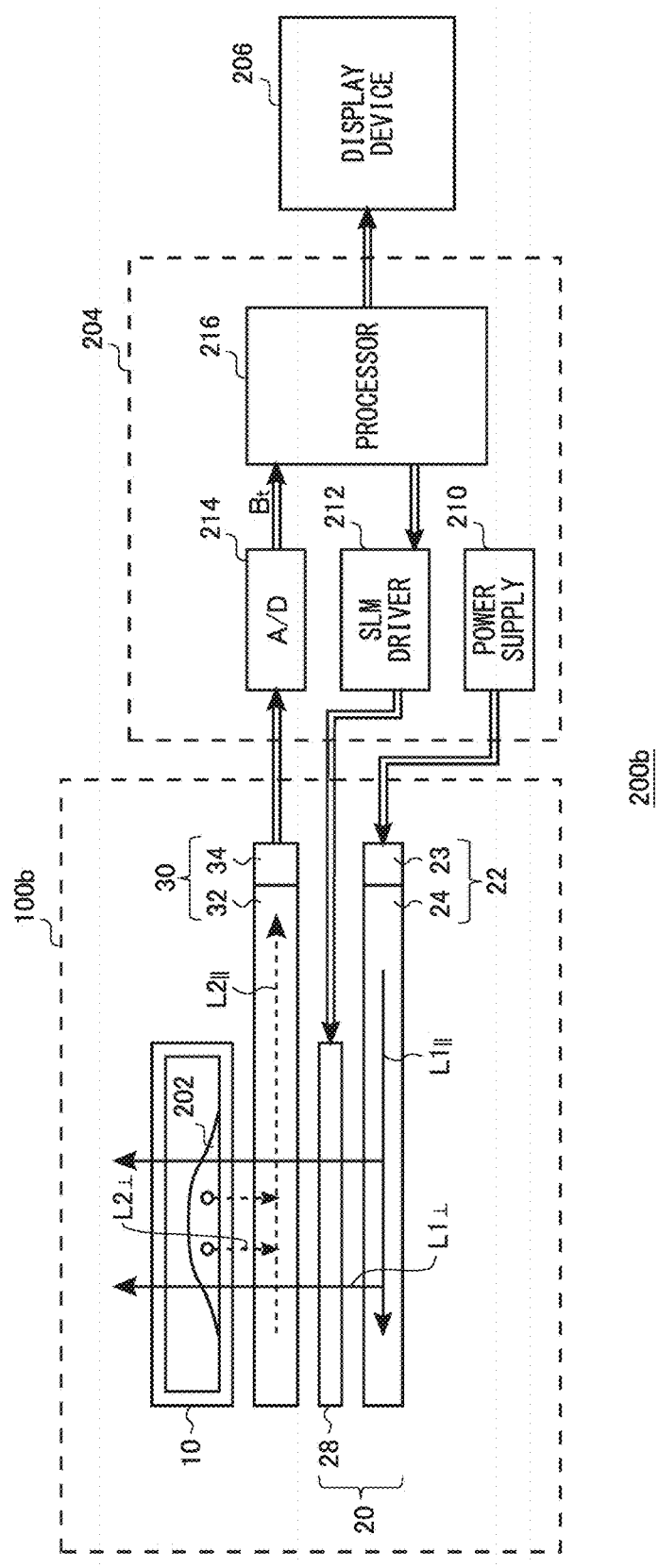
FIG. 11 is a fluorescence microscopy system including a fluorescence microscopy apparatus according to a second embodiment.

FIG. 11 is a diagram showing a fluorescence microscopy system 200b including a fluorescence microscopy apparatus 100b according to a second embodiment. Description will be made mainly regarding the point of difference from the aforementioned embodiment. In the fluorescence microscopy apparatus 100b shown in FIG. 11, the order in which the illumination device 20, the sample holder 10, and the light receiving unit 30 are arranged is modified as compared with an arrangement shown in FIG. 2. That is to say, the first optical member 32 of the light receiving unit 30 is arranged such that it is interposed between the sample holder 10 and the illumination device 20. The first optical member 32 is configured to be transmissive for the excitation light $L1_\perp$. The sample 202 is irradiated from the lower side thereof by the excitation light $L1_\perp$ that has passed through the first optical member 32. The first optical member 32 receives the fluorescence light $L2_\perp$ emitted from the sample 202 toward the lower side (in the Z-axis direction).

The second embodiment provides the same advantages as those of the first embodiment. In another embodiment, the configuration shown in FIG. 2 may be geometrically reversed. Also, the configuration shown in FIG. 11 may be geometrically reversed. Also, as the flat-panel light source 22, a surface-emitting laser such as a VCSEL may be employed.

Third Embodiment

Figure 12A:
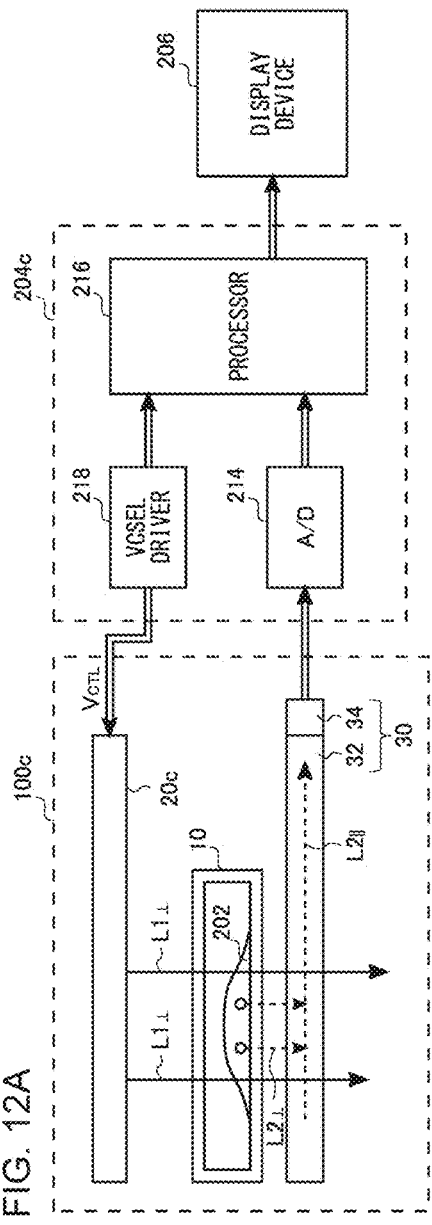
FIGS. 12A and 12B are diagrams each showing a fluorescence microscopy system including a fluorescence microscopy apparatus according to a third embodiment.
Figure 12B:
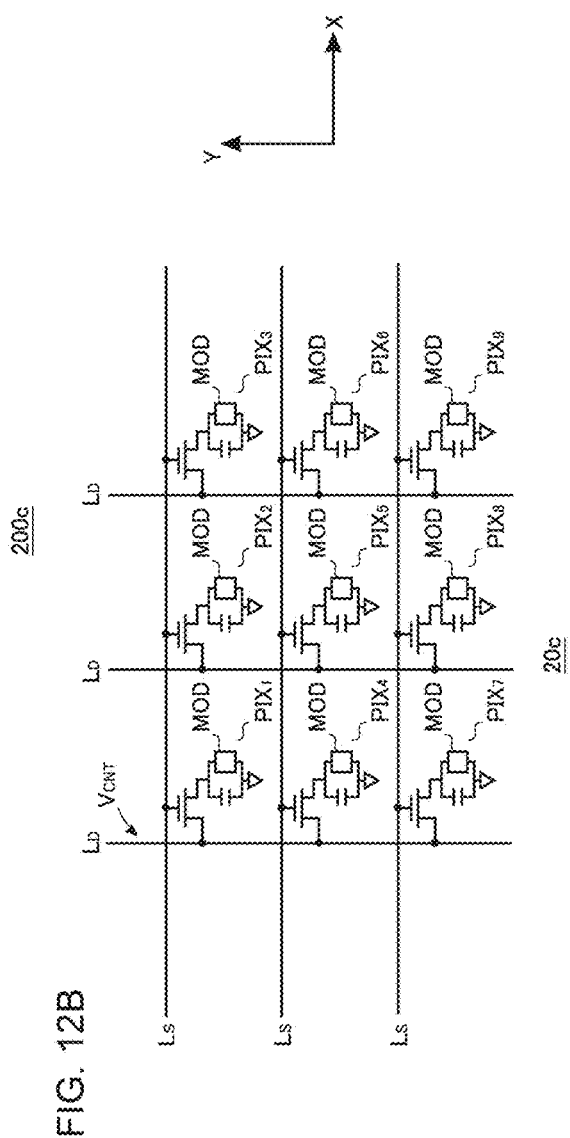

FIGS. 12A and 12B are diagrams each showing a fluorescence microscopy system 200c including a fluorescence microscopy apparatus 100c according to a third embodiment. The fluorescence microscopy apparatus 100c includes an illumination device 20c instead of a combination of the flat-panel light source 22 and the spatial light modulator 28. The illumination device 20c has an output face arranged in parallel with the sample face 12, and is configured as an array of light-emitting elements that are capable of respectively outputting excitation light $I_1$ through $I_N$ which are modulated independently. As shown in FIG. 12B, the illumination device 20c includes multiple pixels $PIX_1$ through $PIX_N$ (N=9 in this example for simplification), and is configured to independently control the amplitude or otherwise the phase of the output light for each pixel. The light-emitting element of each pixel may include a VCSEL. A phase modulator (or otherwise frequency modulator) MOD is formed in each pixel PIX.

For example, an optical crystal may be arranged at the laser beam window of the VCSEL that corresponds to each pixel. Also, different control voltages $V_{CNT}$ may be applied to the respective optical crystals by means of matrix switches so as to modulate the phase of the light to be emitted from each VCSEL. Alternatively, the oscillation frequency (wavelength) to be applied to each VCSEL may be independently controlled for each VCSEL according to the control voltage $V_{CNT}$. This is equivalent to performing phase modulation for each VCSEL, thereby allowing the intensity distribution on the sample face 12 to be controlled. It should be noted that known techniques may be employed to provide the method for electrically controlling the wavelength for each VCSEL. That is to say, such a method is not restricted in particular.

A VCSEL driver 218 of the controller 204c supplies the control voltage $V_{CNT}$ to each VCSEL cell based on the modulation pattern. The method for supplying the control voltage $V_{CNT}$ to the modulator MOD of each pixel is not restricted in particular. Also, the VCSEL may be driven by means of a combination of the scanning lines $L_S$ and the data line $L_D$ as with a matrix display.

With the third embodiment, this arrangement allows the illumination device 20 to have a thin structure as with the first embodiment. This allows the fluorescence microscopy apparatus 100c to have a reduced thickness.

Fourth Embodiment

Figure 13A:
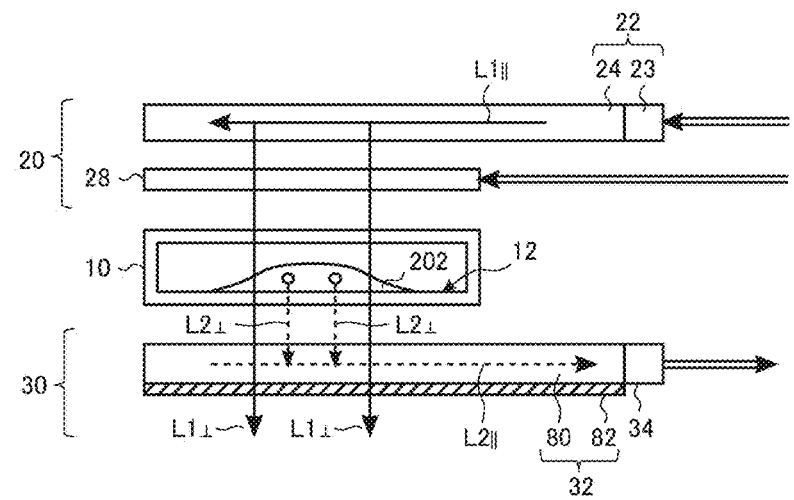
FIGS. 13A and 13B are diagrams each showing a fluorescence microscopy apparatus according to a fourth embodiment.
Figure 13B:
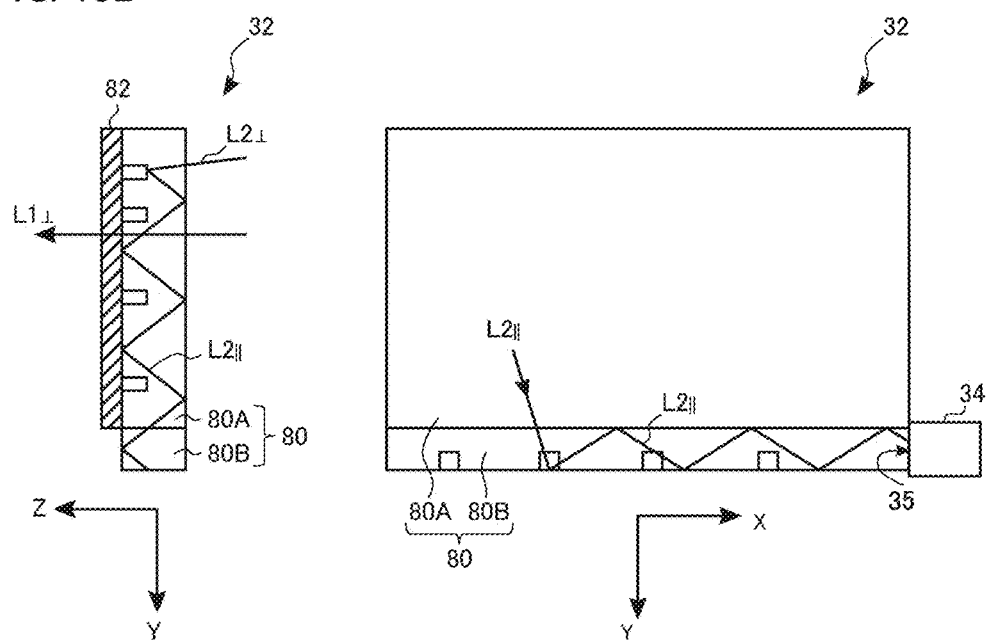

FIGS. 13A and 13B are diagrams each showing a fluorescence microscopy apparatus 100d according to a fourth embodiment. As shown in FIG. 13A, the fluorescence microscopy apparatus 100d has the same basic configuration as that of the fluorescence microscopy apparatus 100a shown in FIG. 2. However, the fluorescence microscopy apparatus 100d employs a light guide plate 80 as the first optical member 32 instead of the input waveguide grating 40. As a backlight for a liquid crystal display, such a light guide plate 80 is employed in order to disperse local light so as to emit light with high uniformity over the plane thereof. Conversely, in the present embodiment, the light guide plate 80 is employed in order to focus the light dispersing on a plane to a local region.

FIG. 13B shows a cross-sectional view and a plan view of the light guide plate 80. The light guide plate 80 includes a first portion 80A and a second portion 80B adjacent to each other in the Y-axis direction. The first portion 80A receives the fluorescence light $L2_\perp$ from the sample 202, guides the fluorescence light thus received toward the second portion 80B in the Y-axis direction. The second portion 80B receives the fluorescence light $L2_\parallel$ that propagates in the Y-axis direction from the first portion 80A, guides the fluorescence light thus received in the X-axis direction, and inputs the fluorescence light thus guided to the photodetector 34. It should be noted that the light guide plate 80 has no wavelength selectivity as its original function. Accordingly, not only the fluorescence light L2, but also the excitation light L1 can enter the photodetector 34. In order to solve such a problem, a transparent reflection layer 82 configured to selectively reflect the fluorescence light L2 and to be transmissive for the excitation light L1 is formed on the back face of the first portion 80A of the light guide plate 80. The reflection layer 82 may be formed as a dielectric multi-layer film. Alternatively, as another approach, the light guide plate 80 may be configured to have no waveform selectivity. Instead, an excitation light cut filter may be arranged between the light guide plate 80 and the light receiving face 35 of the photodetector 34.

With the fourth embodiment, this arrangement allows the light receiving unit 30 to have a thin structure as with the first embodiment. This allows the fluorescence microscopy apparatus 100d to have a reduced thickness.

Fifth Embodiment

Figure 14:
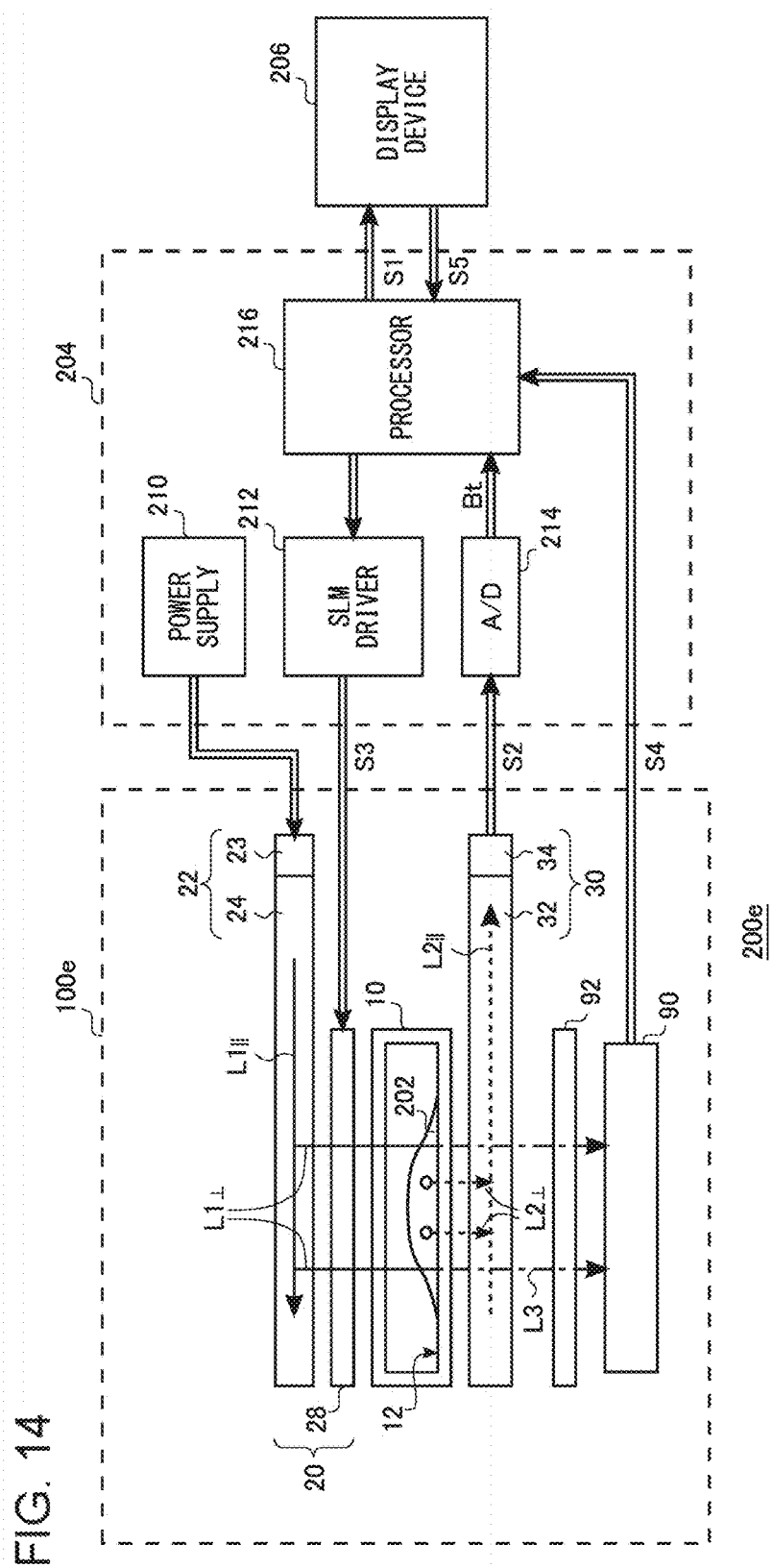
FIG. 14 is a fluorescence microscopy system including a fluorescence microscopy apparatus according to a fifth embodiment.

Description will be made in the fifth embodiment regarding a fluorescence microscopy system 200e that is capable of acquiring a holographic image in addition to a fluorescence image. FIG. 14 is a diagram showing the fluorescence microscopy system 200e including a fluorescence microscopy apparatus 100e according to the fifth embodiment. The fluorescence microscopy apparatus 100e further includes an image sensor 90 for generating a holographic image and a fluorescence cut filter 92 in addition to the fluorescence microscopy apparatus 100a shown in FIG. 2.

The image sensor 90 is arranged on a side that is opposite to the illumination device 20 across the sample holder 10 and the first optical member 32. The image sensor 90 measures the two-dimensional intensity distribution of the light L3 modulated due to the sample 202. As the image sensor 90, a CCD (Charge Coupled Device) or a CMOS (Complementary Metal Oxide Semiconductor) sensor may be employed. The first optical member 32 allows the light L3 to pass through after it is modulated due to the sample 202. It should be noted that, in a case in which the fluorescence light L2 enters the image sensor 90, this leads to degraded image quality of the holographic image. In order to solve such a problem, in a case in which the fluorescence light L2 leaks from the back face of the light receiving unit 30, the fluorescence cut filter 92 is preferably arranged as an additional member.

In the present embodiment, the light L3 modulated due to the sample 202 is the transmitted light of the excitation light $L1_\perp$ that passes through the sample 202. As described above, the first optical member 32 is regarded as being transparent for the excitation wavelength $\lambda_1$. Accordingly, the modulated light L3 enters the image sensor 90 with low loss. In a case in which the sample 202 is an amplitude object, the light L3 is a light obtained by spatially amplitude-modulating the excitation light $L1_\perp$. In this case, the image acquired by the image sensor 90 represents the shape of the object. In a case in which the sample 202 is a phase object, the light L3 is a light obtained by spatially phase-modulating the excitation light $L1_\perp$. In this case, the phase information with respect to the sample 202 is obtained by calculation based on the image acquired by means of the image sensor 90.

Description will be made below assuming that the sample 202 is a phase object. An output S4 of the image sensor 90 is configured as two-dimensional image data I(x, y), which is used to generate a holographic image S5 of the sample 202. Specifically, the processor 216 of the controller 204 generates the holographic image S5 based on the output S4 of the image sensor 90 using a known or prospectively available algorithm. The display device 206 is also used to display the holographic image S5.

The above is the configuration of the fluorescence microscopy apparatus 100e. Next, description will be made regarding the operation thereof. In a mode for measuring the holographic image S5, the phase of the excitation light $L1_\perp$ is set to be uniform. For example, the phase is set to zero for each of all the pixels. In this state, the excitation light $L1_\perp$ to be input onto the sample face 12 is regarded as a plane wave.

Description will be made assuming that the sample 202 is a phase object such as cells. The phase object has a transmissivity of 1, and has a phase characteristic that changes according to the coordinate position. With the phase distribution of the sample 202 as φ(x', y'), the complex amplitude of the light immediately after it passes through the sample 202 (i.e., phase-modulated light L3) is represented by Expression (4). With the distance between the sample 202 and the image sensor 90 as z, the phase distribution on the image sensor 90 is represented by Expression (5). The value I(x, y) detected by the image sensor 90 is represented by Expression (6).

Figure 15:
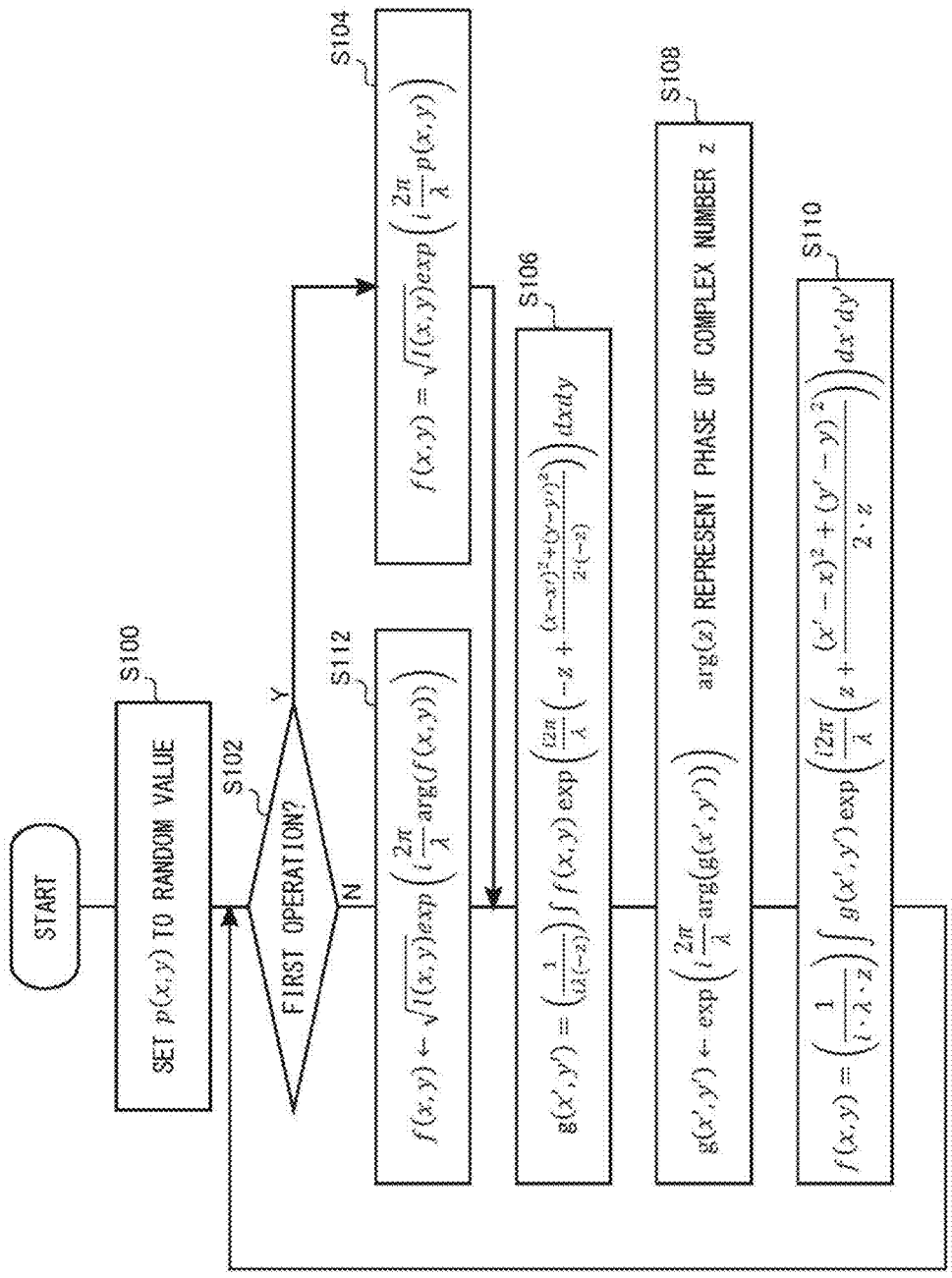
FIG. 15 is a flowchart showing a phase retrieval algorithm.

The processor 216 reproduces the original phase information φ(x', y') based on I(x, y) using a phase retrieval method, for example. FIG. 15 is a flowchart showing a phase retrieval algorithm. First, the predicted values of the phase distribution φ are set to random values (S100). In the first operation (YES in S102), the complex amplitude f(x, y) of the light on the image sensor 90 is calculated based on the amplitude of the light $\sqrt{I(x, y)}$ and the phase information p(x, y). Subsequently, the calculated complex amplitude f(x, y) is subjected to calculation that represents the propagation of the light over the distance z in the reverse direction, thereby calculating the complex amplitude g(x', y') on the sample face 12 (S106).

In a case in which the sample 202 is a phase object, the amplitude is uniform over the sample face 12. Accordingly, the amplitude information is removed from the g(x', y'), and amplitude normalization is performed (S108).

The complex amplitude g(x', y') on the sample face 12 thus obtained is subjected to calculation that represents the propagation of the light over the distance z, thereby calculating the complex amplitude f(x, y) on the image sensor 90 (S110). Subsequently, the flow returns to Step S102. In the second or subsequent operation (NO in S102), the new complex amplitude f(x, y) on the image sensor 90 is calculated based on the amplitude of the light $\sqrt{I(x, y)}$ and the phase component of the complex amplitude f(x, y) obtained in the immediately previous step S110 (S112). Subsequently, the calculated complex amplitude f(x, y) is subjected to calculation that represents the propagation of light over the distance z in the reverse direction, thereby calculating the complex amplitude g(x', y') on the sample face 12 (S106). Subsequently, the same operation is repeatedly performed.

When the aforementioned operation is repeatedly performed, g(x', y') becomes closer to the phase information φ of the sample 202. When calculation convergence is obtained, arg(g(x', y')) is calculated, thereby generating the phase distribution φ(x', y') to be obtained, i.e., thereby generating a holographic image to be obtained.

Figure 16A:
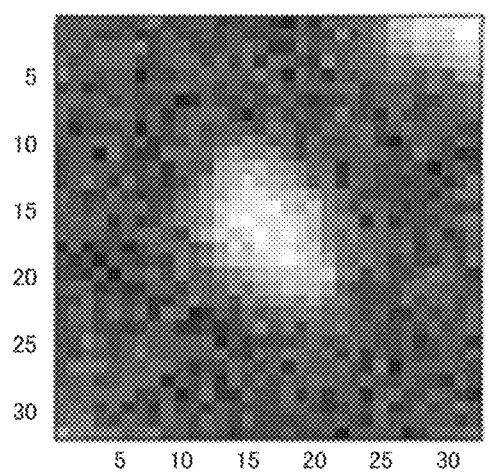
FIG. 16A is a fluorescence image of cells.
Figure 16B:
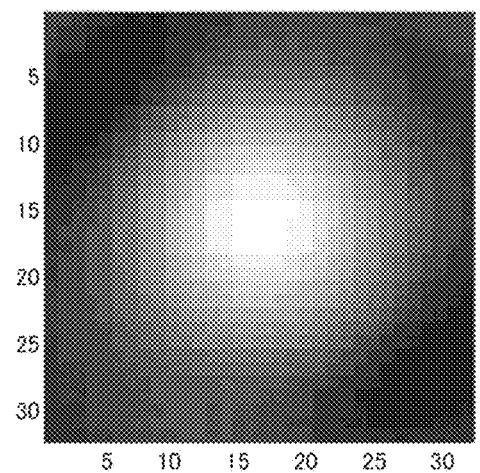
FIG. 16B is a diagram showing an image I(x, y) output from an image sensor.
Figure 16C:
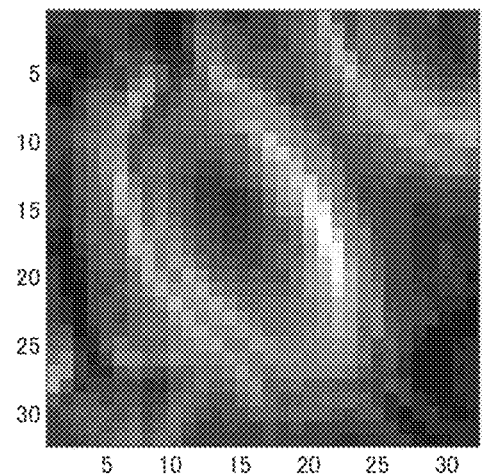
FIG. 16C is a diagram showing phase information φ(x', y') calculated using a phase retrieval method.
Figure 16D:
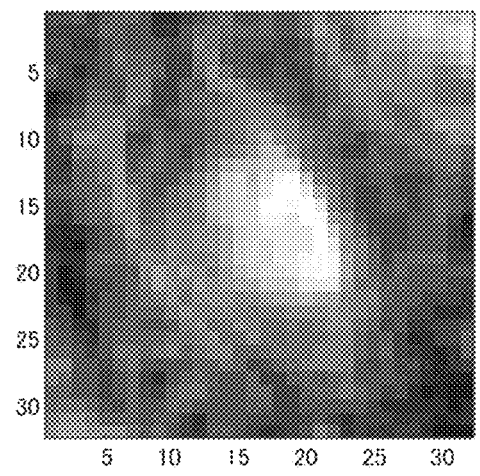
FIG. 16D is a diagram showing a superimposed image obtained by superimposing the phase information φ(x', y') on the fluorescence image acquired using a ghost imaging method.

In a case in which cells are employed as the sample, in many cases, a fluorescent protein expressed in the cells is observed as a fluorescence image. FIG. 16A shows an example of the fluorescence image of cells. Such a fluorescence image does not allow the user to obtain information with respect to the shape of each cell and to obtain information with respect to the portion of the cell where the fluorescence light is emitted. In contrast, by acquiring the phase information in the form of a holographic image, this arrangement allows the user to obtain information with respect to the shape of the cells. As described in the fifth embodiment, by acquiring a holographic image and acquiring a fluorescence image using the ghost imaging method, and by generating a superimposed image based on them, this arrangement allows the user to obtain information on which portion of the cells emits light. FIG. 16B is a diagram showing the image I(x, y) output from the image sensor 90. FIG. 16C is a diagram showing the phase information φ(x', y') calculated using the phase retrieval method. FIG. 16D is a diagram showing the superimposed image obtained by superimposing the phase information φ(x', y') on the fluorescence image acquired using the ghost imaging method.

The fluorescence microscopy apparatus 100e does not require an optical system having a large thickness such as a prism or the like unlike conventional techniques as described in Patent document 1. This arrangement allows the device to have a compact size and a small thickness.

Furthermore, the excitation light L1 that passes through the sample 202 is employed as the light that reflects the phase information with respect to the sample 202. This allows a single excitation light source to be shared by an excitation light source for generating a holographic image and an excitation light source for generating a florescence image. This arrangement allows the configuration of the device to be further simplified, and the size thereof to be further reduced.

Sixth Embodiment

Figure 17:
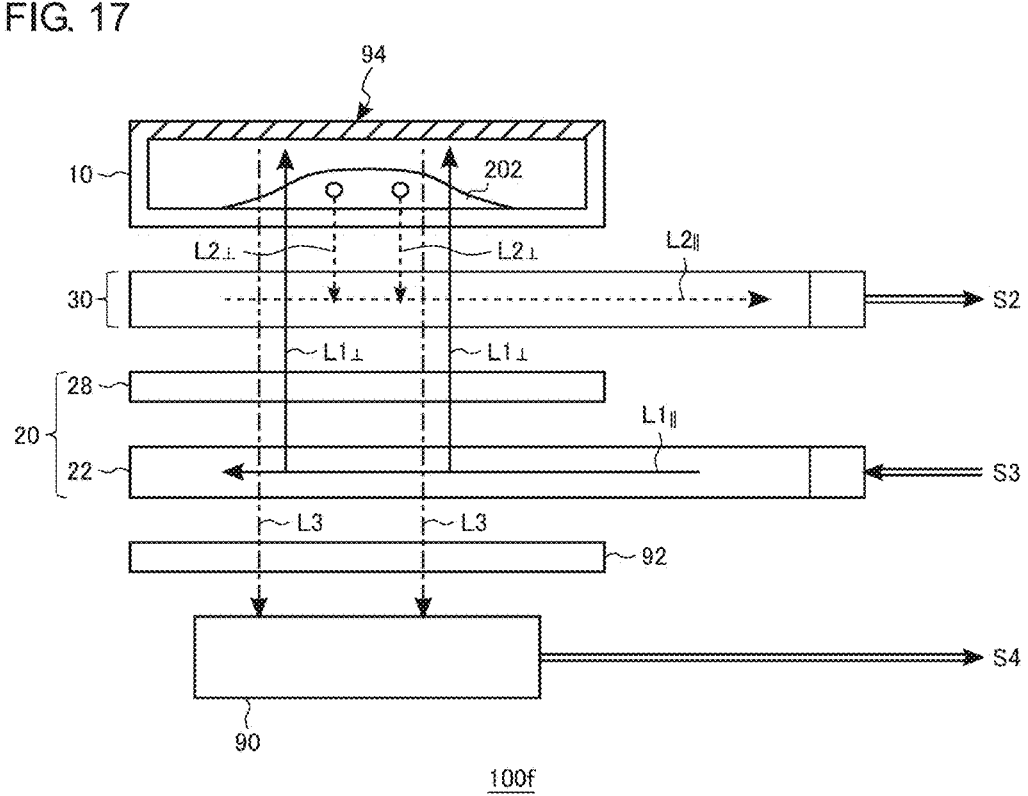
FIG. 17 is a diagram showing a fluorescence microscopy apparatus according to a sixth embodiment.

FIG. 17 is a diagram showing a fluorescence microscopy apparatus 100f according to a sixth embodiment. The fluorescence microscopy apparatus 100f can be regarded as a combination of the fluorescence microscopy apparatus 100b shown in FIG. 11 and the fluorescence microscopy apparatus 100e shown in FIG. 14. In this configuration, a reflection layer 94 or otherwise a mirror is formed on the upper face of the sample holder 10 so as to reflect the excitation light $L1_\perp$.

The excitation light $L1_\perp$ emitted from the illumination device 20 passes through the sample 202, which is a phase object. After the excitation light $L1_\perp$ undergoes phase shifting, the excitation light is reflected by the reflection layer 94 arranged on the upper face of the sample holder 10, and passes through the sample 202 again. Accordingly, the excitation light undergoes phase shifting again. Subsequently, the excitation light passes through the light receiving unit 30 and the illumination device 20, and enters the image sensor 90.

The fluorescence microscopy apparatus 100f is capable of providing the same effects as those of the fluorescence microscopy apparatus 100e shown in FIG. 14.

Figure 18:
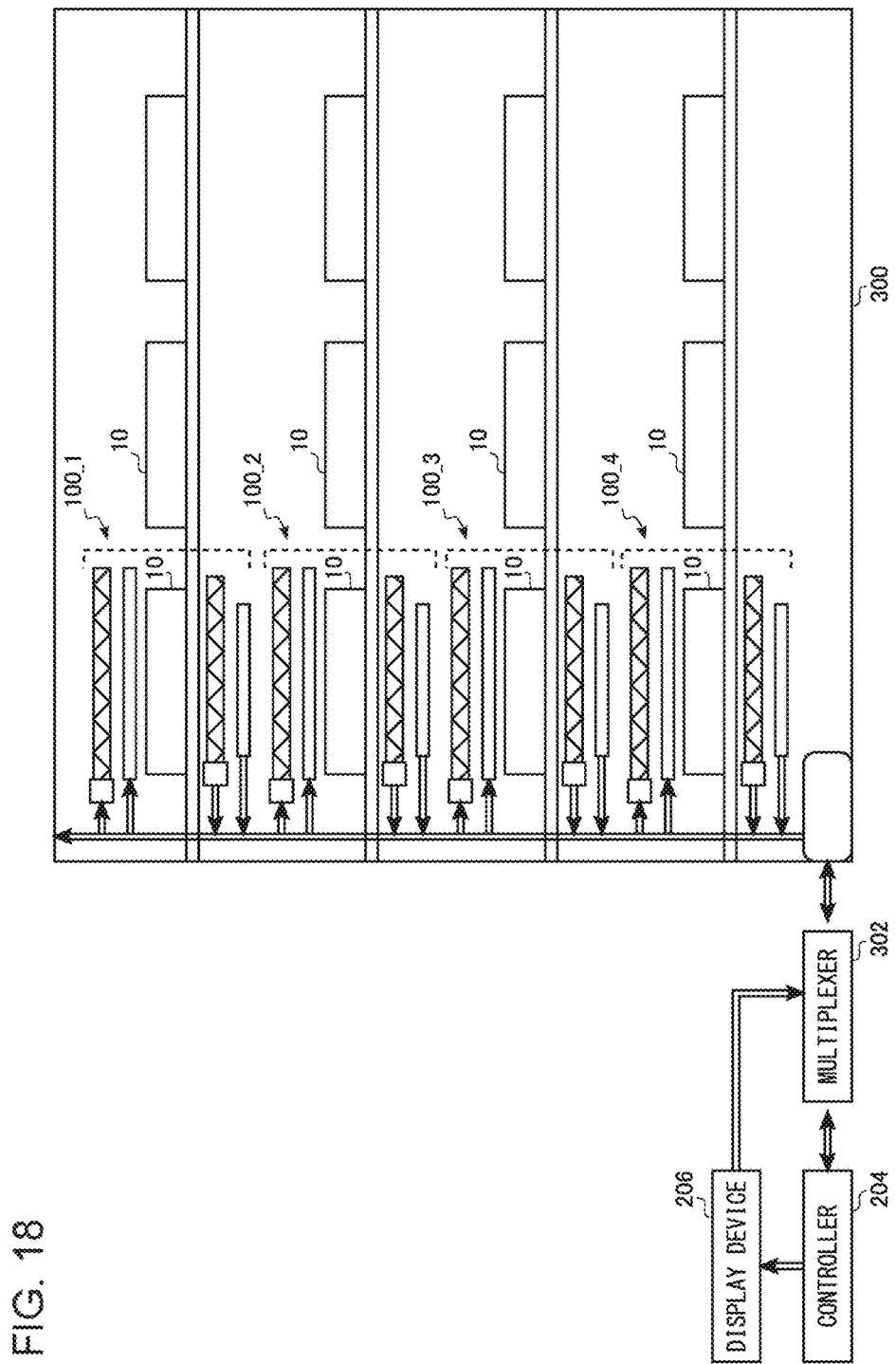
FIG. 18 is a diagram showing an incubator including the fluorescence microscopy apparatus.

FIG. 18 is a diagram showing an incubator including the fluorescence microscopy apparatus 100. An incubator 300 includes a single or multiple fluorescence microscopy apparatuses 100 in addition to a mechanism that adjusts the temperature and humidity. The controller 204 is shared by the multiple fluorescence microscopy apparatuses 100 using a multiplexer 302. FIG. 18 shows an arrangement employing the fluorescence microscopy apparatuses 100a shown in FIG. 2. Also, the fluorescence microscopy apparatuses 100 to be employed may be configured according to another embodiment.

For example, the incubator 300 includes K racks (K=4 in FIG. 18) arranged in the height direction. Each rack houses single or multiple sample holders 10. Furthermore, single or multiple fluorescence microscopy apparatuses 100 are provided for every rack.

By reducing the size of each fluorescence microscopy apparatus 100, this arrangement allows the fluorescence microscopy apparatuses 100 to be easily integrated with an incubator. This means that the user is able to observe cells or the like while cultivating the cells or the like in the incubator. In a case in which such cells are taken out of an incubator, this leads to change in the temperature or humidity around the cells, which is undesirable. Also, in a case in which such cells are taken out of the incubator, this leads to an increase in the risk of cells going missing, the risk of cells falling, or the like. The incubator 300 shown in FIG. 18 can solve such problems.

By employing such thin fluorescence microscopy apparatuses 100, in a case in which the incubator has the same height, this arrangement allows a greater number of fluorescence microscopy apparatuses 100 to be embedded in the incubator. Alternatively, in a case in which the same number of fluorescence microscopy apparatuses are to be embedded in the incubator, by employing such thin fluorescence microscopy apparatuses 100, this arrangement allows the incubator 300 to have a reduced height.

It should be noted that the fluorescence microscopy apparatus 100 (except for the sample holder 10) may be provided for every sample holder 10. Alternatively, a single fluorescence microscopy apparatus 100 may be shared by multiple sample holders 10. In this case, the user may manually transfer each sample holder 10 or otherwise the fluorescence microscopy apparatus 100. Also, a movable stage may be provided so as to relatively change the positions of each sample holder 10 and the fluorescence microscopy apparatus 100.

Also, single or multiple components may be shared by multiple fluorescence microscopy apparatuses 100. Specifically, in a case in which multiple fluorescence microscopy apparatuses 100 are provided to the same rack (step), the illumination device 20 or the light receiving unit 30 may be shared by the multiple fluorescence microscopy apparatuses 100. Alternatively, in a case in which multiple fluorescence microscopy apparatuses 100 are provided over multiple racks in an overlapping manner, the illumination device 20 or the light receiving unit 30 may be shared by the multiple fluorescence microscopy apparatuses 100.

Description has been made above regarding the the present invention with reference to the embodiments. The above-described embodiments have been described for exemplary purposes only, and are by no means intended to be interpreted restrictively. Rather, it can be readily conceived by those skilled in this art that various modifications may be made by making various combinations of the aforementioned components or processes, which are also encompassed in the technical scope of the present invention.

For example, description has been made in the several embodiments (e.g., see FIGS. 1, 2, 11, 12, etc.) regarding an arrangement in which the light receiving face 31 of the light receiving unit 30 and the sample face 12 are arranged in parallel with each other such that they face each other. However, the present invention is not restricted to such an arrangement. In a case in which the light receiving unit 30 has a slope of a large angle with respect to the sample face 12, this leads to a large height of the light receiving unit 30 in the Z-axis direction. However, in a case in which the slope angle is not very large, in some cases, an increase in the height of the light receiving unit 30 in the Z-axis direction does not become a large problem. Accordingly, the light receiving face 31 and the sample face 12 are not required to be arranged perfectly in parallel with each other. Instead, the light receiving face 31 and the sample face 12 may be arranged substantially in parallel with each other. As an example, with a perfectly parallel state as 0°, the light receiving face 31 and the sample face 12 may be arranged in a range between −20° and 20°.

With the first embodiment (FIG. 2), in a case in which the input waveguide grating 40 as shown in FIGS. 3 through 5 is employed as the first optical member 32 of the light receiving unit 30, this arrangement has the potential to involve a situation in which the incident angle (which will be represented by $\theta_{c1}$) at which fluorescence light having a wavelength $\lambda_1$ can couple with the input waveguide grating 40 is close to 0°, which is the incident angle (which will be represented by $\theta_{c2}$) at which fluorescence light having a wavelength $\lambda_2$ can couple with the input waveguide grating 40. In this case, by tilting the light receiving face 33 (input waveguide grating 40) with respect to the sample face 12, the incident angle of the excitation light $L1_\perp$ can be changed away from $\theta_{c1}=0°$, thereby preventing the excitation light $L1_\perp$ coupling with the input waveguide grating 40. In contrast, the fluorescence light $L2_\perp$ can be regarded as spherical waves emitted from an array of point light sources distributed over the sample face 12. Accordingly, even if the light receiving face 33 is tilted, the fluorescence light $L2_\perp$ input in a direction that is orthogonal to the light receiving face 33 (i.e., $\theta_{c2}=0°$) couples with the input waveguide grating 40. Thus, it can be said that the angle between the light receiving face 33 and the sample face 12 has no effect on the measurement of the bucket light. Accordingly, the slope angle between the sample face 12 and the light receiving face 31 of the light receiving unit 30 can be proactively employed as a parameter for controlling the coupling of the fluorescence light and the coupling of the excitation light with the input waveguide grating 40.

In other words, the fluorescence microscopy apparatus 100 according to several embodiments has an advantage that the layout of the sample holder 10, the illumination device 20, and the light receiving unit 30 does not require very severe alignment as compared with fluorescence microscopy apparatuses employing lenses, mirrors, or the like. That is to say, the slope angle between the sample holder 10 and the light receiving unit 30 and the distance between them have substantially no effect on the measurement of the bucket light. Furthermore, the distance z between the illumination device 20 and the sample holder 10 has an effect on the intensity distribution of the excitation light on the sample face 12. However, in actuality, even if the actual distance z deviates from a design value, by correcting z in Expression (5), this problem can easily be solved.

Description has been made in the embodiment regarding the lens-free fluorescence microscopy apparatus 100. However, the present invention is not restricted to such an arrangement. Also, a lens may be employed as a part of the optical members.

The invention claimed is:

1. A fluorescence microscopy apparatus structured to measure a fluorescence image of a sample held by a sample holder, the fluorescence microscopy apparatus comprising:
   an illumination device structured to emit light spatially modulated according to a two-dimensional pattern onto the sample while temporally varying the pattern;
   a first optical member having a light receiving face that faces a sample face, and structured to receive a fluorescence light emitted from the sample via the light receiving face, and to guide the fluorescence light in a direction that is in parallel with the light receiving face; and
   a photodetector structured to receive the fluorescence light guided by the first optical member, and to output a detection signal,
   wherein the detection signal and an intensity distribution formed on the sample face due to the excitation light are acquired for every pattern, and are used to generate the fluorescence image of the sample.

2. The fluorescence microscopy apparatus according to claim 1, wherein the first optical member comprises a waveguide grating structured to selectively couple with the fluorescence light.

3. The fluorescence microscopy apparatus according to claim 1, wherein the first optical member comprises a light guide plate having a back face that is provided with a reflection layer structured to selectively reflect the fluorescence light.

4. The fluorescence microscopy apparatus according to claim 1, wherein the first optical member is arranged on a side that is opposite to the illumination device across the sample holder.

5. The fluorescence microscopy apparatus according to claim 1, wherein the first optical member is arranged between the sample holder and the illumination device, and structured to allow the excitation light to pass through.

6. The fluorescence microscopy apparatus according to claim 1, wherein the illumination device comprises:
an excitation light source structured to emit an excitation light in a direction that is in parallel with the sample face;
a second optical member having a slab waveguide extending substantially in parallel with the sample face, and structured to receive the excitation light via an input face thereof, and to emit the excitation light in the form of a plane wave in a direction that is orthogonal to a direction in which the excitation light is guided; and
a spatial modulator arranged between an output face of the second optical member and the sample holder, and structured to spatially modulate the excitation light configured as the plane wave.

7. The fluorescence microscopy apparatus according to claim 6, wherein the second optical member comprises a waveguide grating.

8. The fluorescence microscopy apparatus according to claim 1, wherein the illumination device comprises an array of light-emitting elements each having an output face which is in parallel with the sample face, and each structured to emit an excitation light which is independently modulated.

9. The fluorescence microscopy apparatus according to claim 8, wherein the light-emitting element comprises a VCSEL (Vertical Cavity Surface Emitting LASER).

10. The fluorescence microscopy apparatus according to claim 6, wherein the intensity distribution formed on the sample face due to the excitation light is obtained by calculation based on a pattern supplied to the spatial light modulator.

11. The fluorescence microscopy apparatus according to claim 1, further comprising an image sensor arranged on a side that is opposite to the illumination device across the sample holder and the first optical member, and structured to measure a two-dimensional intensity distribution of the light modulated due to the sample,
wherein the first optical member allows the light modulated due to the sample to pass through,
and wherein an output of the image sensor is used to generate a holographic image of the sample.

12. The fluorescence microscopy apparatus according to claim 11, wherein the light modulated due to the sample is the excitation light that has passed through the sample.

13. A fluorescence microscopy system comprising:
the fluorescence microscopy apparatus according to claim 1; and
a processor arranged as an external component of the fluorescence microscopy apparatus,
wherein the processor generates a fluorescence image of the sample using the detection signal and the intensity distribution output from the fluorescence microscopy apparatus.

14. A fluorescence microscopy system comprising:
the fluorescence microscopy apparatus according to claim 1; and
a processor as an internal component of the fluorescence microscopy apparatus,
wherein the processor generates a fluorescence image of the sample using the detection signal and the intensity distribution.

15. An incubator comprising a plurality of built-in fluorescence microscopy apparatuses according to claim 1.

16. A fluorescence microscopy apparatus structured to measure a fluorescence image of a sample, comprising:
a sample holder structured to hold the sample via a sample face thereof;
an illumination device structured to emit an excitation light spatially modulated according to a two-dimensional pattern onto the sample while temporally varying the pattern; and
a light receiving unit structured to receive a fluorescence light emitted from the sample,
wherein the illumination device, the sample holder, and the light receiving unit are arranged such that an output face of the illumination device, the sample face, and a light receiving face of the light receiving unit are arranged in parallel and overlap.

17. The fluorescence microscopy apparatus according to claim 16, wherein the light receiving unit is arranged on a side that is opposite to the illumination device across the sample holder, and is structured to be transparent for the excitation light,
and wherein the fluorescence microscopy apparatus further comprises an image sensor arranged on a side that is opposite to the illumination device across the sample holder and the light receiving unit, and structured to measure a two-dimensional intensity distribution of the excitation light modulated due to the sample.

* * * * *